(12) United States Patent
Slukvin et al.

(10) Patent No.: US 9,624,470 B2
(45) Date of Patent: Apr. 18, 2017

(54) MULTIPOTENT LYMPHOHEMATOPOIETIC PROGENITOR CELLS

(75) Inventors: Igor I. Slukvin, Verona, WI (US); Maksym A. Vodyanyk, Madison, WI (US); James A. Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 700 days.

(21) Appl. No.: 13/194,623

(22) Filed: Jul. 29, 2011

(65) Prior Publication Data

US 2012/0040362 A1 Feb. 16, 2012

Related U.S. Application Data

(62) Division of application No. 11/520,871, filed on Sep. 14, 2006, now Pat. No. 8,034,613.

(60) Provisional application No. 60/717,168, filed on Sep. 15, 2005.

(51) Int. Cl.
*C12N 5/0789* (2010.01)
*C12N 5/071* (2010.01)
*G01N 33/53* (2006.01)

(52) U.S. Cl.
CPC .... *C12N 5/0647* (2013.01); *C12N 2502/1394* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 5,759,793 A | 6/1998 | Schwartz et al. | |
| 6,018,096 A | 1/2000 | Keating et al. | |
| 6,280,718 B1 | 8/2001 | Kaufman et al. | |
| 7,247,480 B2 | 7/2007 | Waldmann et al. | |
| 7,615,374 B2 | 11/2009 | Vodyanyk et al. | |
| 7,811,821 B2 | 10/2010 | Slukvin et al. | |
| 2002/0131962 A1 | 9/2002 | Waldmann et al. | |
| 2003/0040607 A1* | 2/2003 | Sackstein | 530/395 |
| 2003/0134305 A1* | 7/2003 | Dertinger | G01N 33/5014 435/6.13 |
| 2006/0063255 A1 | 3/2006 | Lebkowski et al. | |
| 2008/0233610 A1 | 9/2008 | Thomson et al. | |

FOREIGN PATENT DOCUMENTS

| | | |
|---|---|---|
| JP | 2004313038 | 11/2004 |
| SE | 531979 C2 | 9/2009 |
| WO | 0136589 A2 | 5/2001 |
| WO | 0151616 A2 | 7/2001 |
| WO | 2006022330 A1 | 3/2006 |
| WO | 2006130651 A2 | 12/2006 |
| WO | 2007095064 A2 | 8/2007 |
| WO | 2008118820 A2 | 10/2008 |

OTHER PUBLICATIONS

Furley AJ et al. 1986. Divergent Molecular Phenotypes of KG1 and KG1a Myeloid Cell Lines. Blood 68: 1101-1107.*
Vodyanik MA et al. 2004. CD43 Defines Early Hematopoietic Progenitors Derived from Human Embryonic Stem Cells (hESC). Blood 104: 3216.*
"Human and Mouse CD Marker Handbook." BD Biosciences. Available online at <https://www.bdbiosciences.com/documents/cd_marker_handbook.pdf>. Retrieved Nov. 10, 2015.*
Choi K-D et al. 2009. Journal of Clinical Investigation 119: 2818-2829. Generation of mature human myelomonocytic cells through expansion and differentiation of pluripotent stem cell-derived lin-CD34+CD43+CD45+ progenitors—supplemental data. Available online at <http://www.jci.org/articles/view/38591/sd/1>. Retrieved Nov. 10, 2015.*
Choi K-D et al. 2009. Stem Cells 27: 559-587. Hematopoietic and endothelial differentiation of human induced pluripotent stem cells—supplemental data. Available online at <http://www.ncbi.nlm.nih.gov/pmc/articles/ PMC2931800/bin/NIHMS231651-supplement-01.pdf>. Retrieved Nov. 10, 2015.*
Nakamura Y et al. 1999. Ex vivo generation of CD34+ cells from CD34− hematopoietic cells. Blood 94: 4053-59.*
Technical Data Sheet; BV510 Mouse Anti-Human CD41a. Becton Dickinson. Available online at <http://www.bdbiosciences.com/ds/pm/tds/563250.pdf>. 2 pages. Last accessed Jul. 1, 2016.*
Iguchi T et al. 1999. HGF activates signal transduction from EPO receptor on human cord blood CD34+/CD45+ cells. Stem Cells 17: 82-91.*
Wang H-C et al. 2004. Maximum Immunobioactivity of Murine Small Intestinal Intraepithelial Lymphocytes Resides in a Subpopulation of CD43+ T Cells. J Immunol 173: 6294-6302.*
Akashi, et al., A Clonogenic Common Myeloid Progenitor that Gives Rise to All Myeloid Lineages, Nature, 2000, 404:193-197.
Daheron, et al., LIF/STAT3 Signaling Fails to Maintain Self-Renewal of Human Embryonic Stem Cells, Stem Cells, 2004, 22:770-778.
Dahlke, et al., The Biology of CD45 and Its Use as a Therapeutic Target, Leukemia & Lymphoma, 2004, 45 (2):229-236.
Forsyth, et al., Telomerase and Differentiation in Multicellular Organisms: Turn It Off, Turn It on, and Turn It Off Again, Differentiation, 2002, 69:188-197.
Ginis, et al., Differences Between Human and Mouse Embryonic Stem Cells, Developmental Biology, 2004, 269:360-380.
Gong, et al., Fusions of Human Ovarian Carcinoma Cells with Autologous or Allogeneic Dendritic Cells Induce Antitumor Immunity, The Journal of Immunology, 2000, 165:1705-1711.
Habibian, et al., The Fluctuating Phenotype of the Lymphohematopoletic Stem Cell with Cell Cycle Transit, J. Exp. Med., 1998, 188:393-398.

(Continued)

*Primary Examiner* — Emily Cordas
(74) *Attorney, Agent, or Firm* — Quarles & Brady, LLP

(57) ABSTRACT

This invention relates to hematopoietic precursors derived from human embryonic stem cells. In the culture of differentiated cells from human ES cells, the fully committed hematopoietic precursors are CD34+ and CD43+ but not CD45+. If the cells are cultured until they express CD45, then the cells lose the ability to produce differentiated cells of the lymphoid lineages.

3 Claims, 23 Drawing Sheets

(56) References Cited

OTHER PUBLICATIONS

Kaufman, et al., Hematopoietic Colony-Forming Cells Derived from Human Embryonic Stem Cells, Proc. Natl. Acad. Sci. USA, 2001, 98:10716-10721.
Li, et al., Hematopoietic Differentiation In Vitro of Rhesus Monkey Embryonic Stem Cells, Blood, 1998, 92:368a.
Li, et al., Bone Morphogenetic Protein 4 Induces Efficient Hematopoietic Differentiation of Rhesus Monkey Embryonic Stem Cells In Vitro, Blood, 2001, 98:335-342.
Martin, et al., Differences in Lymphocyte Developmental Potential Between Human Embryonic Stem Cell and Umbilical Cord Blood-Derived Hematopoietic Progenitor Cells, Blood, 2008, 112(7):2730-2737.
Martinez Del Hoyo, et al., Characterization of a Common Precursor Population for Dendritic Cells, Nature, 2002, 415:1043-1047.
Nakano, et al., Generation of Lymphohematopoietic Cells From Embryonic Stem Cells in Culture, Science, 1994, 265:1098-1101.
Odorico, et al., Multilineage Differentiation from Human Embryonic Stem Cell Lines, Stem Cells, 2001, 19:193-204.
Parkhurst, et al., Hybrids of Dendritic Cells and Tumor Cells Generated by Electrofusion Simultaneously Present Immunodominant Epitopes from Multiple Human Tumor-Associated Antigens in the Context of MHC Class I and Class II Molecules, The Journal of Immunology, 2003, 170:5317-5325.
Remold-O'Donnell, et al., Expression on Blood Cells of Sialophorin, the Surface Glycoprotein That Is Defective in Wiskott-Aldrich Syndrome, Blood, 1987, 70(1):104-109.
Ryu, et al., In Vitro Generation of Functional Dendritic Cells from Human Umbilical Cord Blood CD34+ Cells by a 2-Step Culture Method, International Journal of Hematology, 2004, 80:281-286.
Salvagiotto, et al., Molecular Profiling Reveals Similarities and Differences Between Primitive Subsets of Hematopoietic Cells Generated In Vitro from Human Embryonic Stem Cells and In Vivo During Embryogenesis, Experimental Hematology, 2008, 36(10):1377-1389.
Scott-Taylor, et al., Human Tumour and Dendritic Cell Hybrids Generated by Electrofusion: Potential for Cancer Vaccines, Biochimica et Biophysica Acta, 2000, 1500:265-279.
Senju, et al, Generation and Genetic Modification of Dendritic Cells Derived from Mouse Embryonic Stem Cells, Blood, 2003, 101(9):3501-3508.
Shamblott, et al., Human Embryonic Germ Cell Derivatives Express a Broad Range of Developmentally Distinct Markers and Proliferate Extensively In Vitro, Proc. Natl. Acad. Sci. USA, 2001, 98(1):113-118.
Slukvin, et al., Directed Differentiation of Human Embryonic Stem Cells Into Functional Dendritic Cells Through the Myeloid Pathway, The Journal of Immunology, 2006, 176:2924-2932.
Slukvin, et al., Development of Lymphohematopoietic Progenitors During Human Embryonic Stem (hES) Cell Differentiation on OP9 Stromal Cells, Blood (ASH Annual Meeting Abstracts), 2004, 104:Abstract 2789.
Szabolcs, et al., Expansion of Immunostimulatory Dendritic Cells Among the Myeloid Progeny of Human CD34+ Bone Marrow Precursors Cultured with c-kit Ligand, Granulocyte-Macrophage Colony-Stimulating Factor, and TNF-a1,2, The Journal of Immunology, 1995, 154:5851-5861.
Thomson, et al., Embryonic Stem Cell Lines Derived from Human Blastocysts, J. Science, 1998, 282:1145-1147.
Vodyanik, et al., Human Embryonic Stem Cell-Derived CD34+ Cells: Efficient Production in the Coculture with OP9 Stromal Cells and Analysis of Lymphohematopoietic Potential, Blood, 2005, 105(2):619-628.
Vodyanik, et al., Leukosialin (CD43) Defines Hematopoietic Progenitors in Human Embryonic Stem Cell Differentiation Cultures, Blood, 2006, 108(6):2095-2105.
Xu, et al., BMP4 Initiates Human Embryonic Stem Cell Differentiation to Trophoblast, Nature Biotechnology, 2002, 20:1261-1264.
Xu, et al., Basic FGF and Suppression of BMP Signaling Sustain Undifferentiated Proliferation of Human ES Cells, Nature Methods, 2005, 2:185-190.
Zhan, et al., Functional Antigen-Presenting Leucocytes Derived From Human Embryonic Stem Cells In Vitro, Lancet, 2004, 364:163-171.
Help:About, www.wikipedia.com, 1 page, Accessed by Examiner on May 7, 2010.
Swedish Patent Office, Application No. 0702695-8, Office Action (English Translation), Oct. 8, 2008.
Applicant, Swedish Application No. 0702695-8, Response to Oct. 8, 2008 Office Action, Feb. 4, 2009.
European Patent Office, Application No. 06771688.6, Office Action, Feb. 19, 2009.
Applicant, European Patent Application No. 06771688.6, Response to Feb. 19, 2009 Office Action, Dec. 14, 2009.
UK Intellectual Property Office, Application No. GB0816154.9, Examination Report, Oct. 1, 2008.
Applicant, Application No. GB0816154.9, Response to Oct. 1, 2008 Examination Report, Jun. 18, 2009.
UK Intellectual Property Office, Application No. GB0816154.9, Examination Report, Oct. 30, 2009.
UK Intellectual Property Office, Application No. GB0723152.5, Examination Report, Sep. 22, 2009.
Applicant, Application No. GB0723152.5, Response to Sep. 22, 2009, Examination Report, Mar. 19, 2010.
Intellectual Property Office of Singapore, Application No. 200718257-9, Written Opinion, Jan. 19, 2010.
U.S. Appl. No. 11/443,608, Office Action, Sep. 22, 2008.
Applicant, U.S. Appl. No. 11/443,608, Response to Sep. 22, 2008, Non-Final Office Action, Jan. 22, 2009.
U.S. Appl. No. 11/443,608, Office Action, Apr. 17, 2009.
Applicant, U.S. Appl. No. 11/443,608, Response to Apr. 17, 2009, Final Office Action, Sep. 17, 2009.
U.S. Appl. No. 11/443,608, Office Action, Oct. 16, 2009.
Applicant, U.S. Appl. No. 11/443,608, Response to Oct. 16, 2009, Non-Final Office Action, Feb. 16, 2010.
U.S. Appl. No. 11/672,724, Office Action, May 15, 2009.
Applicant, U.S. Appl. No. 11/672,724, Response to May 15, 2009 Non-Final Office Action, Aug. 6, 2009.
U.S. Appl. No. 11/672,724, Office Action, Dec. 17, 2009.
U.S. Appl. No. 12/024,770, Office Action, Dec. 15, 2008.
Applicant, U.S. Appl. No. 12/024,770, Response to Dec. 15, 2008 Non-Final Office Action, Apr. 15, 2009.

* cited by examiner

Figure 1 (A, C)
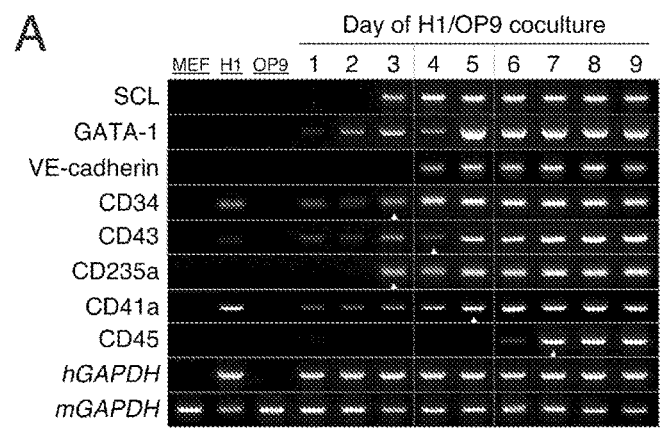
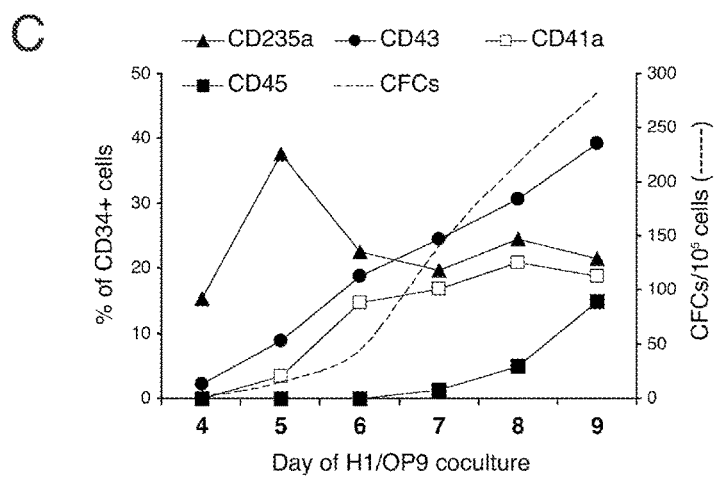

Figure 6 (A, B, D)
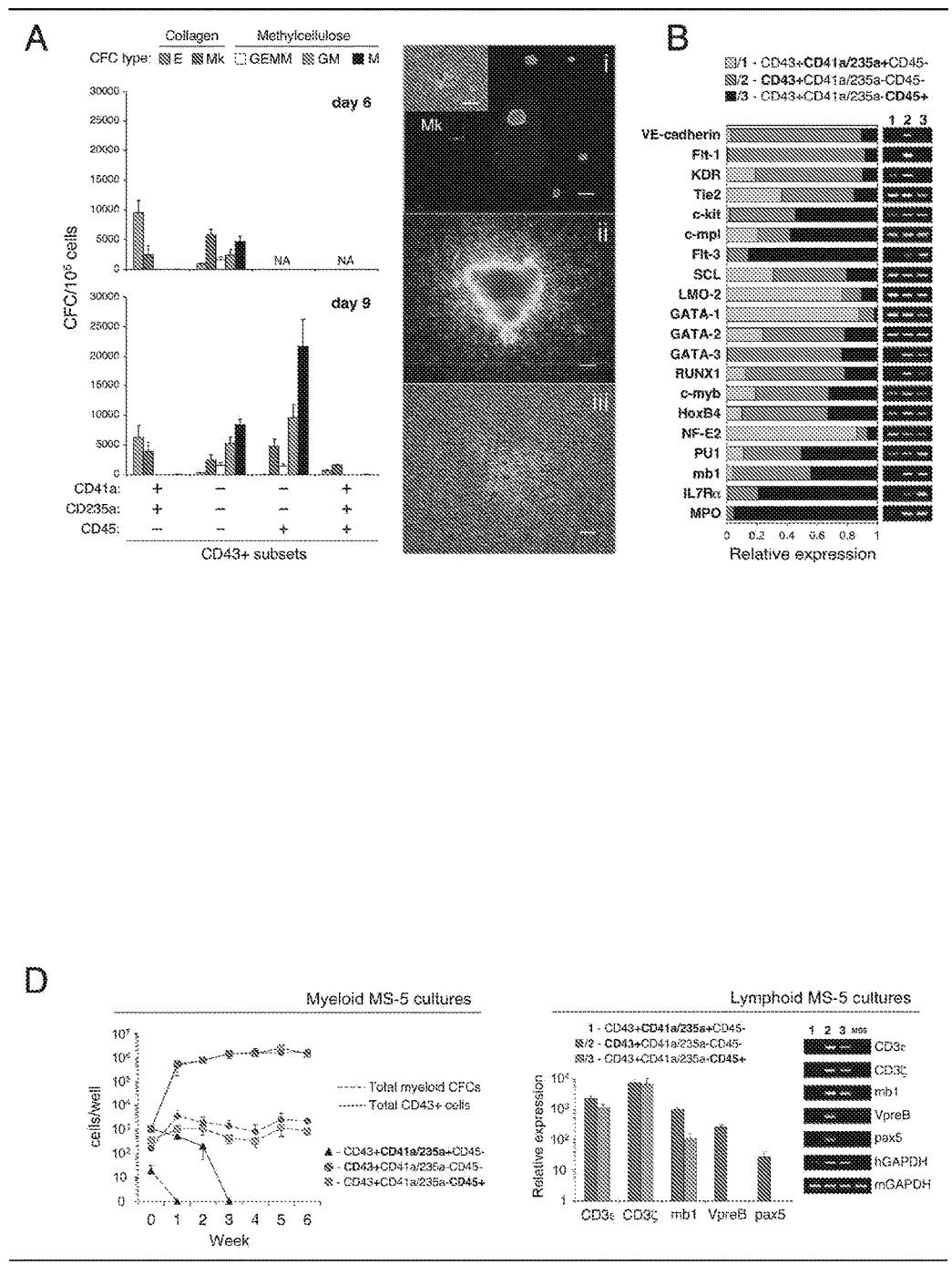

FIGURE 9 (A & B).
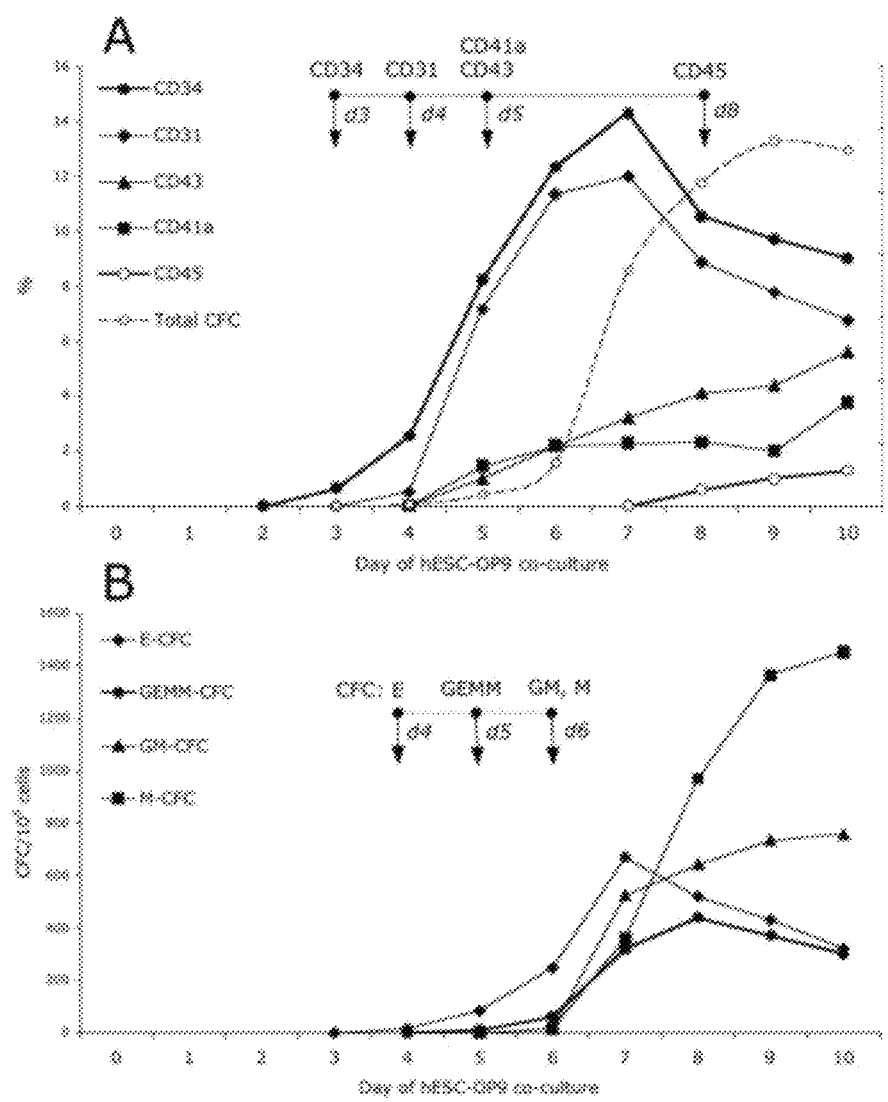

FIGURE 13 (B, C, D).
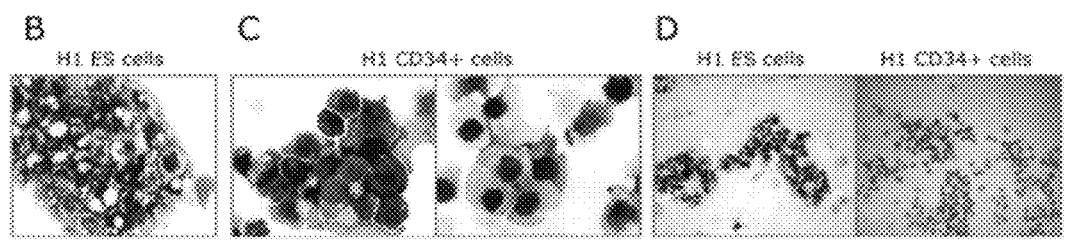

FIGURE 14 (A, B, C, D, E, F, G).
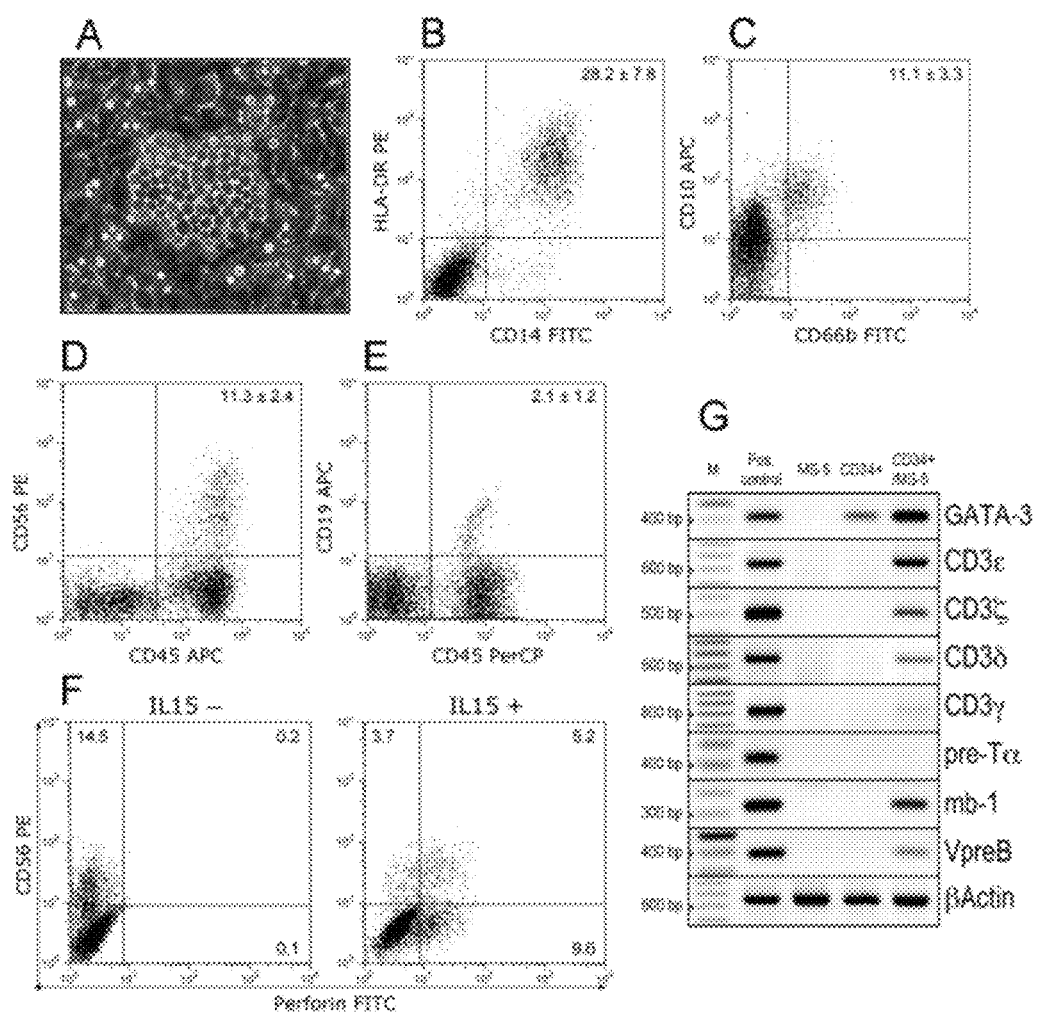

SEQUENCE LISTING

<160> NUMBER OF SEQ ID NOS: 32

<210> SEQ ID NO 1
<211> LENGTH: 21
<212> TYPE: DNA
<213> ORGANISM: Artificial
<220> FEATURE:
<223> OTHER INFORMATION: synthetic oligonucleotide primer

```
<400> SEQUENCE: 1
ttccggtacc tgtgagtcag c                                              21

<210> SEQ ID NO 2
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 2
agttggcgtt tgggggcaag atggtaatga agaaa                               35

<210> SEQ ID NO 3
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 3
gggctgctcc acgcttttgc                                                20

<210> SEQ ID NO 4
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 4
ctctgcctcc cagcctcttt                                                20

<210> SEQ ID NO 5
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 5
ttcaacttat acccttcgtg tc                                             22

<210> SEQ ID NO 6
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 6
atgcacggca tctgggaatc                                                20

<210> SEQ ID NO 7
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 7
caagtgctgt gcatacaatt ccc                                            23

<210> SEQ ID NO 8
<211> LENGTH: 21
```

```
<212> TYPE: DNA
<213> ORGANISM: Artificial
<220> FEATURE:
<223> OTHER INFORMATION: synthetic oligonucleotide primer

<400> SEQUENCE: 8
tccaaaatca agtggggcga t                                        21

<210> SEQ ID NO 9
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 9
ctccctgtcc ccaatagtgc                                          20

<210> SEQ ID NO 10
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 10
gcttccctct ctgaaatagc cgaa                                     24

<210> SEQ ID NO 11
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 11
tgcaggagca gtatcatgaa gcct                                     24

<210> SEQ ID NO 12
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 12
tccaagctct gcctgccacc at                                       22

<210> SEQ ID NO 13
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 13
agtacacagc ccatgcatct gtca                                     24

<210> SEQ ID NO 14
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 14
```

```
atggtgcagc tgagtcctcc                                        20

<210> SEQ ID NO 15
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 15
tttgtctact gcacaggttg tgg                                    23

<210> SEQ ID NO 16
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 16
tgacggggtc acccacactg tgcccatcta                             30

<210> SEQ ID NO 17
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 17
ggtacagttg gtaatggctg c                                      21

<210> SEQ ID NO 18
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 18
cccaggaaac agggagtcgc aggggactgg agag                        34

<210> SEQ ID NO 19
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 19
tttccccaat aggtggcgc                                         19

<210> SEQ ID NO 20
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 20
gcgtcgtagg tgtccttggt                                        20

<210> SEQ ID NO 21
<211> LENGTH: 22
<212> TYPE: DNA
<213> ORGANISM: Artificial
```

```
<220> FEATURE:
<223> OTHER INFORMATION: synthetic oligonucleotide primer

<400> SEQUENCE: 21
cctgctttac tttgtccact tc                                              22

<210> SEQ ID NO 22
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 22
gtcactgtcc tgcaagttgc tgtc                                            24

<210> SEQ ID NO 23
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 23
acctgtacca tctgtagctg g                                               21

<210> SEQ ID NO 24
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 24
ttctagacgg caggtcaggt c                                               21

<210> SEQ ID NO 25
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 25
gtccttcggc tgctcctgtg                                                 20

<210> SEQ ID NO 26
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 26
cagaatctaa gctcgggaca cgtt                                            24

<210> SEQ ID NO 27
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 27
gcatcaaaca actgtggcca gtga                                            24
```

```
<210> SEQ ID NO 28
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 28
gactgctggt atgactcgtt gc                                              22

<210> SEQ ID NO 29
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 29
aatgctccaa gactggagga agga                                            24

<210> SEQ ID NO 30
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 30
tctcattctt gctgagcttc                                                 20

<210> SEQ ID NO 31
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 31
tgcagtgggt tccatttctt cc                                              22

<210> SEQ ID NO 32
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 32
ctagaagctt gcggtggacg atggaggg                                        28
```

MULTIPOTENT LYMPHOHEMATOPOIETIC PROGENITOR CELLS

CROSS-REFERENCE TO RELATED APPLICATIONS

This application is a divisional application of U.S. application Ser. No. 11/520,871 filed Sep. 14, 2006 now U.S. Pat. No. 8,034,613, which claims the benefit of U.S. provisional application 60/717,168, filed Sep. 15, 2005. Both applications are incorporated by reference herein.

STATEMENT REGARDING FEDERALLY SPONSORED RESEARCH OR DEVELOPMENT

This invention was made with government support under W81XWH-04-C-0139 awarded by the DOD/DARPA and HD044067 awarded by the National Institutes of Health. The government has certain rights in the invention.

BACKGROUND OF THE INVENTION

During human and mouse embryogenesis, primary hematopoietic cells are generated in the yolk sac and para-aortic splanchnopleura/aorta-genital ridges-mesonephros (AGM) region; however, only cells generated in the AGM region are believed to contribute to hematopoietic stem cells (Godin I, et al., *Nat Rev Immunol.* 2002; 2:593-604). Both extra- and intra-embryonic hematopoietic cells develop in close association with endothelial cells from common hematoendothelial precursors, which were identified within early embryonic and embryonic stem cell (ESC)-derived cell populations expressing endothelial markers (VEGF-R2 (KDR), VE-cadherin, CD31, Tie2) (Tavian M, et al. *Ann N Y Acad. Sci.* 2005; 1044:41-50; Li W, et al., *Stem Cells Dev.* 2005; 14:44-54; Jaffredo T, et al., *Int J Dev Biol.* 2005; 49:269-277; Fraser S T, et al., *Exp Hematol.* 2002; 30:1070-1078; Wang L, et al., *Immunity,* 2004; 21:31-41; Nishikawa S I, et al., *Development,* 1998; 125:1747-1757; Choi K, et al., *Development* 1998; 125:725-732). These precursors are of particular interest for studies on the divergence of endothelial and hematopoietic cell lineages and establishment of hematopoietic stem cells, however, their identification requires a reliable separation of the earliest lineage-committed progeny, since hematopoietic and endothelial derivatives may share a common phenotype at early stages of development and still may not express typical lineage-specific markers. For example, in the mouse embryo, CD45, the most specific marker of hematopoietic lineage, is not expressed on the earliest hematopoietic progenitors arising in the yolk sac and AGM region; however, these progenitors can be identified by expression of CD41 molecule, which is specific for megakaryocytic lineage in adults (Li W, et al., *Stem Cells Dev.* 2005; 14:44-54; Mikkola H K, et al., *Blood* 2003; 101:508-516; Bertrand J Y, et al., *Proc Natl Acad Sci USA,* 2005; 102:134-139; Ferkowicz M J, et al., *Development* 2003; 130:4393-4403; Mitjavila-Garcia M T, et al., *Development* 2002; 129:2003-2013).

Hematopoietic differentiation of human ESCs (hESCs) reproduces many aspects of embryonic hematopoiesis and provides an in vitro model to elucidate mechanisms of early hematopoietic commitment, (Keller G., *Genes Dev.* 2005; 19:1129-1155; Wang L, et al., *Exp Hematol.* 2005; 33:987-996) practically inaccessible in the human embryo (Tavian M, et al., *Int J Dev Biol.* 2005; 49:243-250). Several hESC hematopoietic differentiation systems based on either coculture with stromal cells (Kaufman D S, et al., Proceedings of the National Academy of Sciences of the United States of America. 2001; 98:10716-10721; Qiu C, et al., *Exp Hematol.* 2005; 33:1450-1458; Vodyanik M A, et al., *Blood* 2005; 105:617-626) or formation of embryoid bodies (Chadwick K, et al., *Blood* 2003; 102:906-915; Zambidis E T, et al., *Blood* 2005; 106:860-870; Ng E S, et al., *Blood* 2005; 106:1601-1603) have been established. Recently, we described hESC differentiation in coculture with OP9 stromal cells that resulted in a highly efficient generation of hematopoietic progenitors after 4-5 days of coculture (Vodyanik M A, et al., *Blood* 2005; 105:617-626). We and others have demonstrated that hematopoietic clonogenic progenitors arise within CD34$^+$ cell population before emergence of CD45$^+$ cells, suggesting that the first hematopoietic progenitors in humans, like in mice, can not be identified by CD45 expression (Kaufman D S, et al., Proceedings of the National Academy of Sciences of the United States of America 2001; 98:10716-10721; Vodyanik M A, et al., *Blood* 2005; 105:617-626; Zambidis E T, et al., *Blood* 2005; 106:860-870; Ng E S, et al., *Blood* 2005; 106:1601-1603).

BRIEF SUMMARY OF THE INVENTION

In the present study, we evaluated expression of specific hematopoietic markers (CD41a, CD43, CD45, CD235a) during hESC differentiation in OP9 coculture. We demonstrated that hESC-derived hematopoietic progenitors could be identified by surface expression of leukosialin (CD43). Selection of CD43$^+$ cells reliably separated CD34$^+$ hematopoietic cells from CD34$^+$CD43$^-$KDR$^+$CD31$^+$ endothelial cells and CD34+CD43–KDR–CD31– mesenchymal cells. Also, CD43 was expressed on erythroid progenitors lacking CD34 expression, thus allowing complete isolation of CD34$^+$ and CD34$^-$ hematopoietic progenitors from hESC/OP9 cocultures. While CD41a was detected on CD43$^+$ cells before CD45, isolation of CD41a$^+$ cells demonstrated that these cells are already committed to erythro-megakaryocytopoiesis.

In addition, we found that the first multipotent lymphohematopoietic progenitors have CD34$^+$CD43$^+$CD45$^-$Lin$^-$ phenotype, coexpress endothelial proteins KDR, VE-cadherin, and CD105, and have Flt-3$^{low}$GATA-3$^{high}$RUNX1$^{high}$ gene expression profile. Acquisition of CD45 expression by CD34$^+$CD43$^+$CD45$^-$Lin$^-$ cells was associated with advanced differentiation toward the myeloid cell lineage.

The present invention is broadly summarized as producing lymphohematopoietic progenitor cells from human embryonic stem cells. As described above, we have found that in the process of differentiation of human embryonic stem cells in culture the cell surface characteristics of the fully functional lymphohematopoietic progenitors do not include expression of the cell surface marker CD45, previously associated with hematopoietic cells in humans.

The present invention is also summarized as a lymphohematopoietic progenitor in which the cells have a phenotype which is CD34+ and CD43+ but CD45– and Lin$^-$, the cells having the potential to form all of the colony-forming cell types and to form lymphoid cells.

The present invention is also summarized as a method for isolating hematopoietic precursors from human embryonic stem cell culture, including isolating cells based on the phenotype of CD34+, CD43+ but CD45– and Lin$^-$.

It is an object of the present invention to define a protocol for the generation of large numbers of human lymphohematopoietic cells for use in scientific research and for potential use in human therapeutics.

Inserts show FACS analysis of respective surface (VE-cadherin) and intracellular (eNOS, vWF) markers in parallel cultures, or instant FACS profiles of cells incubated with DiI-Ac-LDL at 37° C. (Ac-LDL uptake) versus 4° C. (control Ac-LDL binding). (C) Vascular tubes formation by CD34$^+$CD43$^-$KDR$^+$ cells (scale bar is 200 µm, left panel; and 50 µm, right panel). (D) TNF-induced up-regulation of ICAM-1 and induction of VCAM-1 expression in CD34$^+$CD43$^-$KDR$^+$ endothelial cultures. Numbers within plots indicate ΔMFI values for untreated (blue) and TNF-treated (red) cells. VLA-4 staining was used as a control. A representative example of 3 independent experiments is shown.

Figure 5:
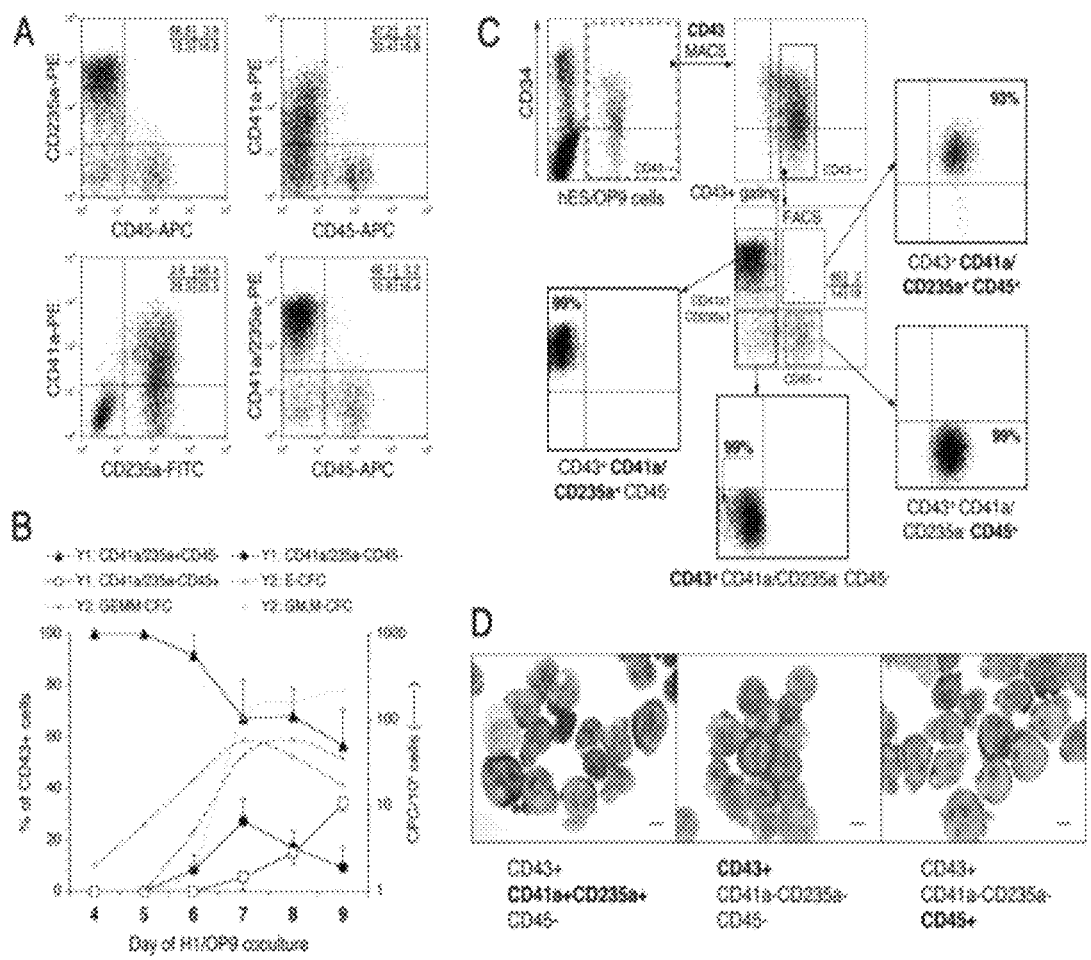

FIG. 5. CD43$^+$ cell subsets: definition, kinetic profile, sorting and morphology. (A) The phenotype of CD43$^+$ cells isolated on day 8 of H1/OP9 coculture. CD41a and CD235a were co-expressed (lower left dot-plot), and both in opposite manner to CD45 (upper dot-plots). Combination of CD41a-OE, CD235a-OE and CD45-APC mAbs (lower right dot-plot) defines three major CD43$^+$ subsets: (1) CD43$^+$CD41a/CD235$^+$CD45$^-$, (2) CD43$^+$CD41a/CD235a$^-$CD45$^-$, and (3) CD43$^+$CD41a/CD235a$^-$CD45$^+$. Values within plots indicate % of cells in respective quadrants. Representative analysis is shown. (B) Kinetic analysis of indicated CD43$^+$ subsets in H1/OP9 coculture represented as % of total CD43$^+$ cells (left Y1-axis). Dashed trend lines show parallel kinetics of indicated CFC types (right Y2-axis). Results are the mean±SD from 3 independent experiments. (C) Sorting strategy employed for isolation of CD43$^+$ subsets. A representative example of 7 independent experiments is shown (H1, n=5; H9, n=2). (D) Wright-stained cytospins of FACS-sorted CD43$^+$ subsets (scale bar is 5 µm).

FIG. 6. Phenotypic and functional analysis of CD43$^+$ subsets. (A) CFC potential of FACS-sorted CD43$^+$ subsets on day 6 and day 9 of hESC/OP9 cocultures. E/Mk– and GEMM/GM/M-CFCs were determined by serum-free collagen assay and FBS-containing MethoCult GF+ methylcellulose assay, respectively. Results are the mean±SD from 9 independent experiments (H1, n=6; H9, n=3). NA indicates not applicable (subset was not detected/sorted). Photographs show typical E- and small Mk-colonies detected in CD43$^+$CD41a/CD235a$^+$CD45$^{-/+}$ subsets (i, scale bar is 200 µm; insert shows Mk-colony stained with anti-CD41a mAb, scale bar is 50 µm), and typical multilineage GEMM (ii, scale bar is 200 µm) and large Mk-colonies (iii, scale bar is 50 µm) detected in CD43$^+$CD41a/CD235a$^-$CD45$^{-/+}$ subsets. (B) FACS analysis of CD43$^+$ subsets. CD43$^+$ cells were isolated on day 8 of H1/OP9 coculture by direct CD43 MACS MicroBeads. Color-matching combinations of CD43, CD41a, CD235a, CD45 and indicated mAbs were used for CD43$^+$ subset gating and analysis. Plots show isotype control (open) and specific mAb (tinted) histograms. Values within plots indicate ΔMFI values. Representative analysis of 3 independent experiments is shown. (C) qRT-PCR analysis of FACS-sorted CD43$^+$ subsets on day 8 of H1/OP9 coculture. The stacked bar graph shows expression levels of indicated transcripts represented by relative units. Results are the means of 2 independent experiments. Representative agarose gel electrophoresis of qPCR products is shown. (D) Lymphoid and myeloid differentiation of FACS-sorted CD43$^+$ subsets in coculture with MS-5 stromal cells. CD43$^+$ subsets were isolated on day 8 of hESC/OP9 cocultures and cultured with MS-5 cells in presence of cytokines supporting either lymphoid or myeloid differentiation. Lymphoid MS-5 cultures were examined for expression of NK– (CD3ε, CD3ζ) and B-cell (mb1, VpreB, pax5) specific transcripts by qRT-PCR on the 4$^{th}$ week of culture. The relative expression of each GAPDH-normalized target gene was calculated in comparison with isolated CD3ε/ζ$^+$ cells before coculture (mb1, very low levels of CD3ε/ζ; but no detectable VpreB and pax5 were found in CD43$^+$ cells before coculture). Results are the mean±SD from 3 independent experiments with H1 (n=2) and H9 (n=1) cells. A representative agarose gel of PCR products is shown. Myeloid MS-5 cocultures were examined for total CD43$^+$ cells and myeloid CFCs (GM/M) during 6 weeks of culture. Results are the means±SD from 4 independent experiments (H1, n=2; H9, n=2).

Figure 7:
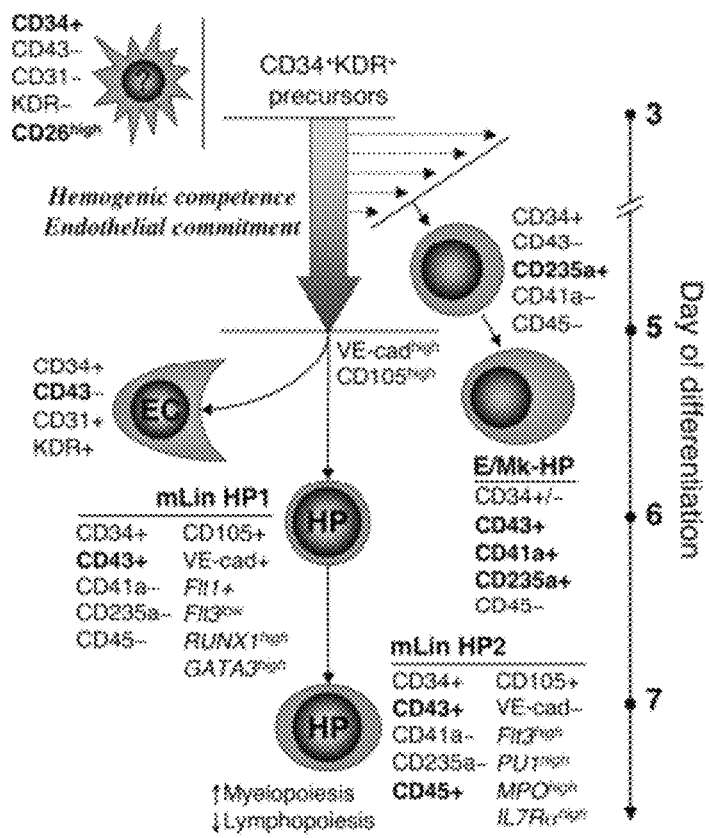

FIG. 7. A model of hematoendothelial differentiation in hESC/OP9 coculture. Hematopoietic and endothelial cells develop from early precursors identified by a CD34$^+$KDR$^+$ (CD43$^-$) phenotype. These precursors appear at day 3 of differentiation and retain hematoendothelial potential up to day 5, but after 6 days, CD34$^+$CD43$^-$KDR$^+$ cells constitute a population of committed endothelial cells (EC). CD43 is identified as a specific marker of early hematopoietic progenitors. Two types of CD43$^+$ hematopoietic progenitors are identified in hESC/OP9 coculture: (1) CD43$^+$CD41a/CD235a$^+$ erythro-megakaryocytic progenitors (E/Mk-HP) first detectable on day 4 of differentiation, and (2) CD43$^+$CD41a/CD235a$^-$ multilineage (mLin) progenitors (HP1) appeared two days later. Emergence of E/Mk-HP before mLin HP1 and residual expression of VE-cadherin, Flt1 and CD105 endothelial markers by HP1 cells may reflect a step-wise endothelial commitment of CD34$^+$KDR$^+$ hematoendothelial precursors (block arrow): CD34$^+$KDR$^+$ precursors at initial pre-endothelial commitment stage are only competent to generate E/Mk-HP through CD235$^+$ intermediates, while multipotent HP1 are derived from CD34$^+$KDR$^+$ precursors with an endothelial phenotype (VE-cadherin$^{high}$CD105$^{high}$). HP1 have lymphomyeloid potential and a gene expression profile found in the most immature hematopoietic progenitors. HP1 transition to CD45$^+$ stage (HP2) is associated with progressive myeloid commitment and a decrease of lymphoid potential. CD34$^+$CD43$^-$KDR$^-$CD26$^{high}$ cells arise along with the first CD34$^+$KDR$^+$ cells and may comprise more than 20% of total CD34$^+$ cells in hESC/OP9 cocultures. These cells are devoid of detectable hematoendothelial potential.

Figure 8:
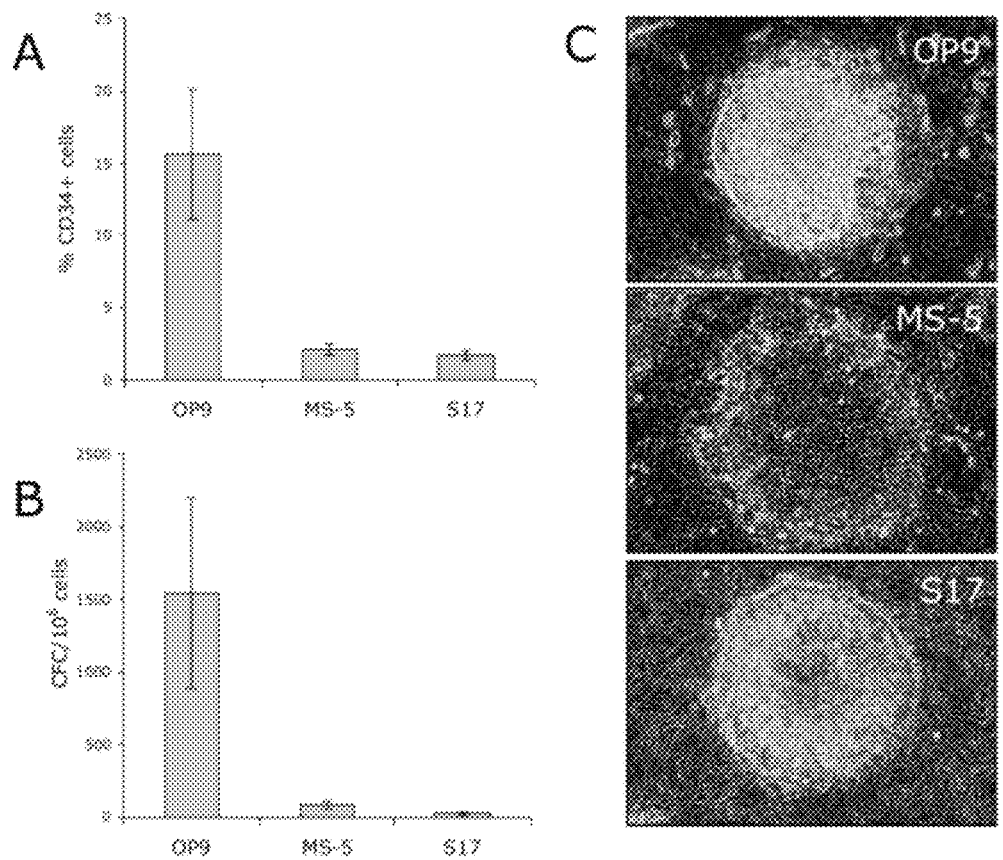

FIG. 8. Distinct hemogenic properties of OP9 cell line. Induction of CD34+ expression (A) and CFCs (B) after 7 days of co-culture of H1hES cells on OP9, MS-5, and S17 bone marrow stromal cell lines. Results are mean±SD of 3 experiments±SD. (C) Morphology of differentiated hES cell colonies after 4 days of co-culture with OP9, MS-5, and S17 cells (original magnification is 40×).

Figure 9C:
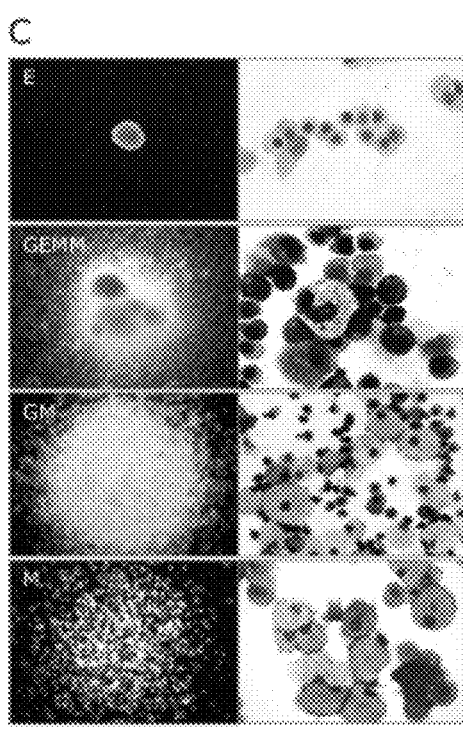

FIG. 9. Induction of hematopoietic molecules and CFCs during hES cells/OP9 co-culture. (A) Percentages of CD34+, CD31+, CD43+, CD41a$^+$, and CD45+ cells (left Y-scale) as determined by flow cytometry, and total numbers of CFCs (right Y-scale) in hES cell/OP9 co-culture at days 1-10. Day 0 indicates undifferentiated hES cells. (B) Kinetic of different CFC types in hES cell/OP9 co-culture. A and B figures represent mean results from 6 experiments (H1=3; H9=3); arrows on the top of each figure point to the earliest day when expression of indicated markers or CFCs was detectable. (C) Morphology (left column), and Wright staining of cytospins (right column) of different CFC types. Left column: original magnification is 40×. Right column: E-CFC, GEMM-CFC (original magnification is 1000×), GM-CFC, and M-CFC (original magnification is 400×).

Figure 10:
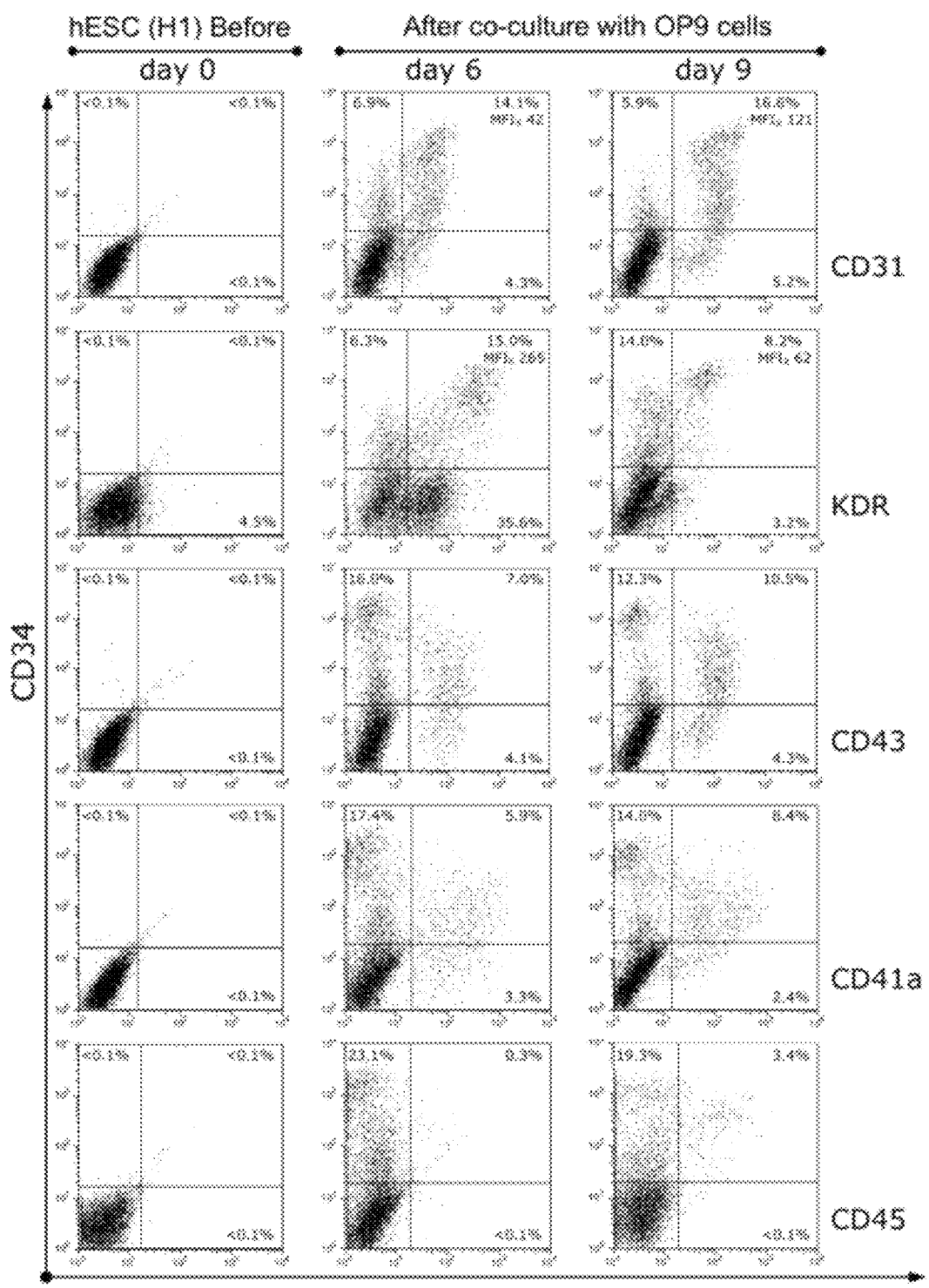

FIG. 10. Sequential phenotypic analysis of differentiated hES cells in OP9 co-culture. Representative phenotype of undifferentiated (day 0), and differentiated H1hES cells on day 6, and day 9 of OP9 co-culture. Single cell suspension from hES cell/OP9 co-culture obtained at indicated time was labeled with CD34 (Y-axis) and with CD31, KDR, CD43 CD41a or CD45 mAbs as indicated in right corner of each row (X-axis). Numbers indicate percentages of positive cells and MFI (X-scale) in corresponding quadrants.

Figure 11:
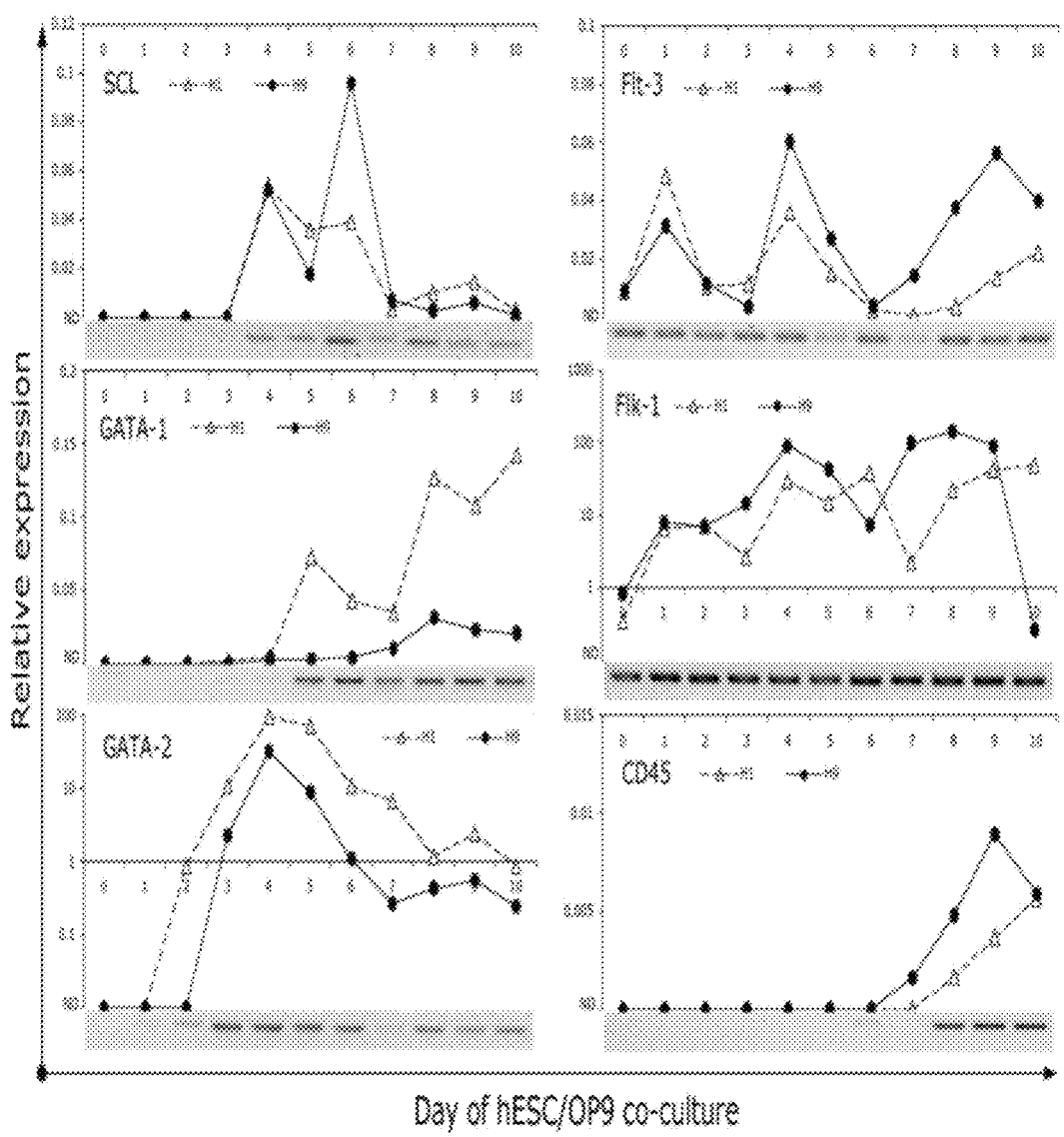

FIG. 11. Kinetic analysis of hematopoiesis-associated gene expression by QRT-PCR. Human-specific primers listed in Table 1 were used to amplify indicated genes during H1 and H9 differentiation in OP9 co-culture. Pictures under each graph show corresponding agarose gel electrophoresis of QPCR from H1 cell samples. Gene expression relative to bone marrow RNA was calculated using $\Delta\Delta Ct$ method.

Figure 12:
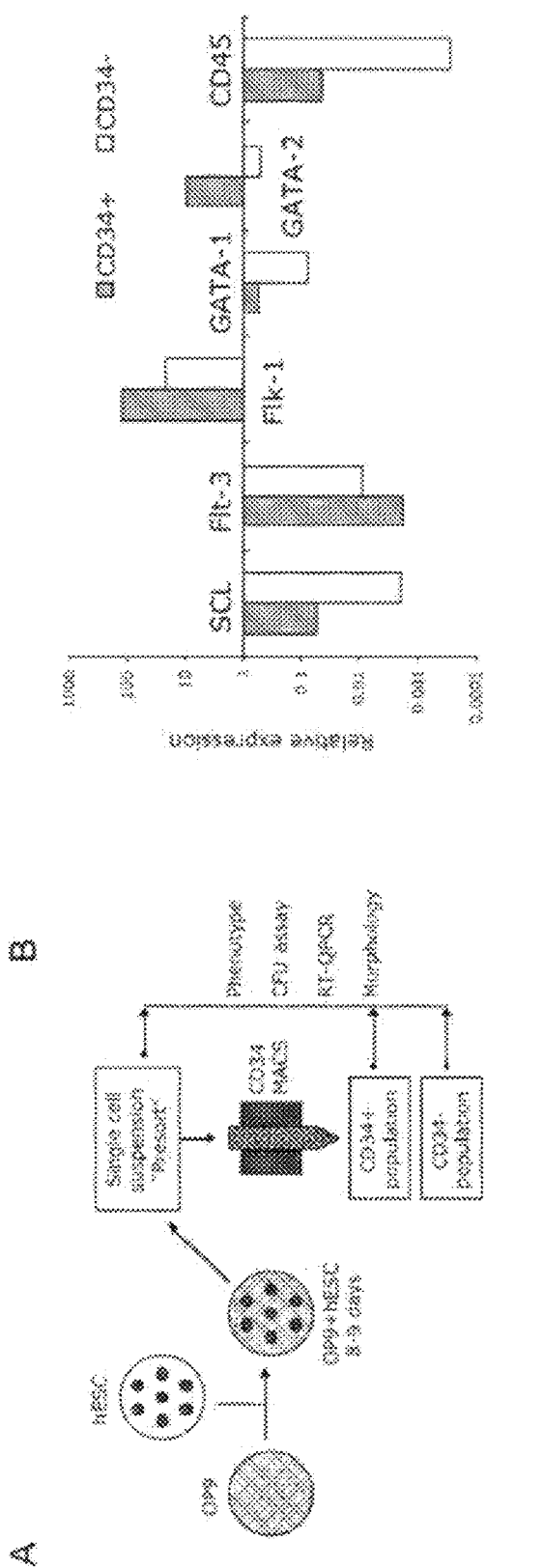
Figure 12:
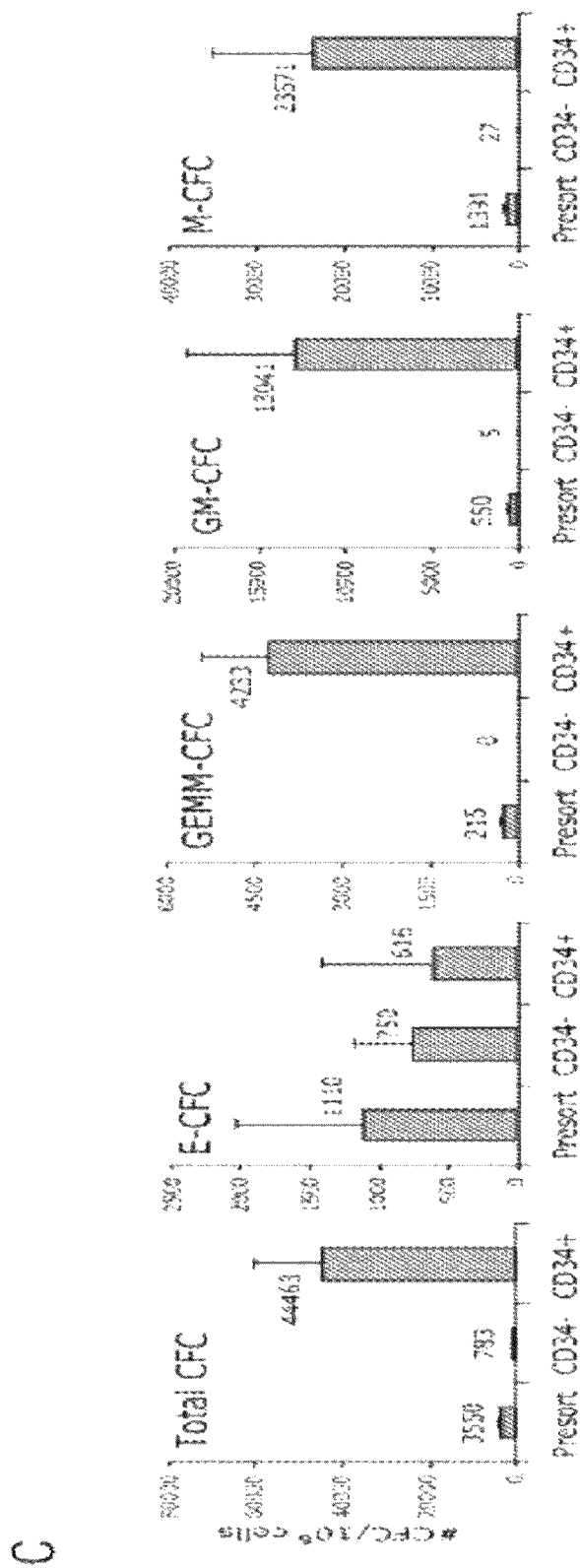
Figure 12:
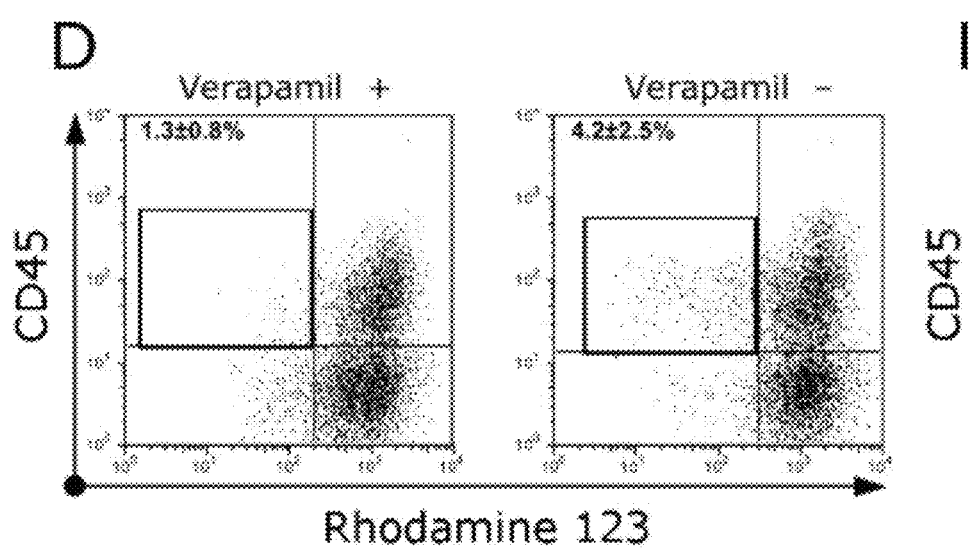
Figure 12:
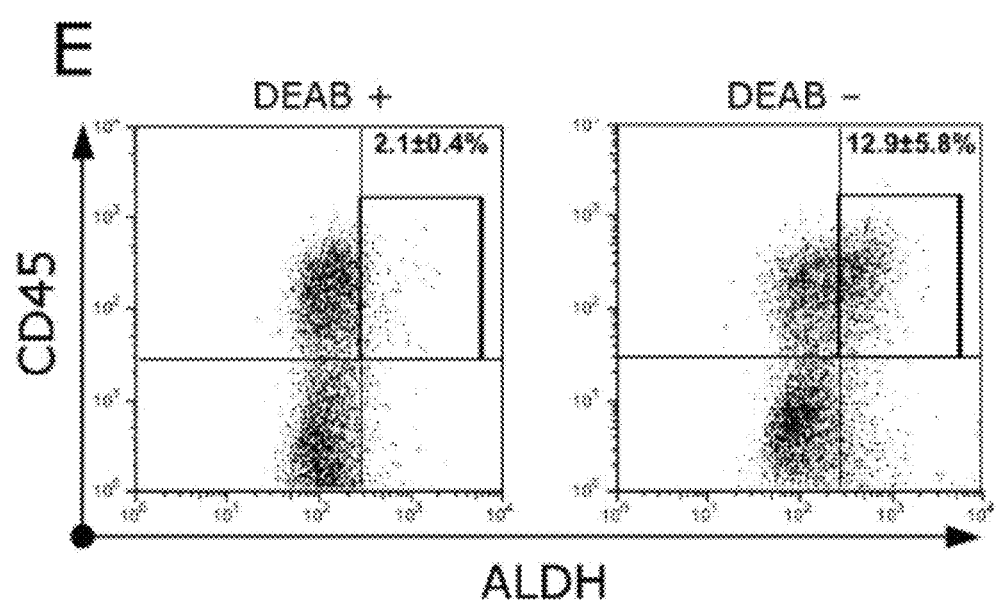

FIG. 12. Isolated CD34+ cells revealed hematopoietic progenitor potential. (A) Schematic diagram of the protocol used for CD34+ cells isolation and analysis. (B) Relative expression of hematopoiesis-associated genes in CD34+ and CD34− populations by QPCR. (C) Clonogenic potential of H1CD34+ and CD34− cells. Results are mean±SD of 4 experiments. (D) Rho efflux and CD45 expression by isolated CD34+ cells were analyzed by flow cytometry. The gates used to distinguish $Rho^{low}$ population of CD34+ CD45+ cells and percentages of $Rho^{low}$ cells within this gate (mean±SD of 3 experiments; H1=2, H9=1) are indicated. (E) ALDH and CD45 expression by isolated CD34+ cells were analyzed by flow cytometry. The gates used to distinguish the $ALDH^{high}$ population of CD34+CD45+ cells and percentages of $ALDH^{high}$ cells within this gates (mean±SD of 3 experiments; H1=2, H9=1) are indicated.

FIG. 13. Phenotype and morphology of undifferentiated hES cells and hES cell-derived CD34+ cells. (A) Comparative expression of hematopoiesis-associated surface molecules on undifferentiated hES cells (upper row) and isolated CD34+ cells (lower row). Depicted histograms represent H1 cells, MFI values in the right histogram corner are mean±SD of 9 experiments (H1=6, H9=3). (B) Morphology of Wright stained cytospins of undifferentiated H1hES cells (original magnification is 1000×). (C) Wright stained cytospins of isolated H1 CD34+ cells demonstrate two different populations (original magnification is 1000×). (D) Oct-4 immunostaining of undifferentiated H1 ES cells and H1-derived CD34+ cells (original magnification is 200×). CD34+ cells are Oct-4 negative.

FIG. 14. Development of myeloid, NK and B cells from hES cell-derived CD34+ cells. CD34+ cells were cultured on MS-5 stromal cells as described in Materials and Methods. (A) CD34+ cells gave rise to phase-dark cobblestone-shaped colonies underneath the stroma starting from day 7 of co-culture (original magnification is 200×). (B)-(F) Phenotype of the cells generated after 21 days of CD34+/MS-5 co-culture. Flow cytometric analysis demonstrated presence of CD14+HLA-DR+ macrophages (B) and CD66b+CD10+ mature granulocytes (C) within CD45+ gated population. In addition, CD56+CD45+ NK cells (D), and CD19+CD45+ B cell precursors (E) were evident. Numbers in the upper right corner indicate percentages of positive cells in the corresponding quadrant (mean±SD of 4 experiments; H1=2, H9=2). (F) IL-15 induced expression of perforin in CD56+ cells. CD34+ cells were cultured on MS-5 cells without (left panel) or with IL-15 (right panel). Cells were stained with CD56-PE and CD45-APC mAbs followed by permeabilization and staining with perforin-FITC mAbs. Dot plots represent CD45+ gated cells. (G) Analysis of gene expression in isolated CD34+ cells and cells after 21 days of CD34+/MS-5 co-culture by RT-PCR. Positive controls are as follows: human bone marrow (GATA-3); peripheral blood lymphocytes (CD3ε, CD3δ, CD3γ, CD3ζ); thymus (pre-Tα); fetal liver (mb-1, VpreB). Transcripts of the studied genes were not amplified from MS-5 cells alone. M-DNA markers (100 bp ladder).

DETAILED DESCRIPTION OF THE INVENTION

1. In General

During hematopoietic differentiation of human embryonic stem cells (hESC), early hematopoietic progenitors arise along with endothelial cells within CD34+ population. Although hESC-derived hematopoietic progenitors have been previously identified by functional assays, their phenotype has not been defined. Herein, using hESC differentiation in coculture with OP9 stromal cells, we demonstrate that early progenitors committed to hematopoietic development can be identified by surface expression of leukosialin (CD43).

As described below in the Examples, CD43 was detected on all types of emerging clonogenic progenitors before expression of CD45, persisted on differentiating hematopoietic cells, and reliably separated the hematopoietic CD34+ population from CD34+CD43−CD31+KDR+ endothelial and CD34+CD43−CD31−KDR− mesenchymal cells. Furthermore, we demonstrated that the first-appearing CD34+ CD43+CD235a+CD41a+/−CD45− cells represent pre-committed erythro-megakaryocytic progenitors. Multipotent lymphohematopoietic progenitors were generated later as CD34+CD43+CD41a−CD235a− CD45− cells. These cells were negative for lineage-specific markers (Lin−), expressed KDR, VE-cadherin and CD105 endothelial proteins, and GATA-2, GATA-3, RUNX1, c-myb transcription factors that typify initial stages of definitive hematopoiesis originating from endothelial-like precursors. Acquisition of CD45 expression by CD34+CD43+CD45− Lin− cells was associated with progressive myeloid commitment and a decrease of B-lymphoid potential. CD34+CD43+CD45+Lin− cells were largely devoid of VE-cadherin and KDR expression, and had a distinct $Flt3^{high}GATA3^{low}RUNX1^{low}PU1^{high}$ $MPO^{high}IL7R\alpha^{high}$ gene expression profile.

2. Specific Embodiments of the Invention

Cell Populations

The hematopoietic precursors of the present invention are capable of generating the full range of cell types in the hematopoietic lineage, including the lymphoid lineage. By "full range of hematopoietic cells" we mean: red blood cells, megakaryocytes and white blood cells, including lymphocytes, polymorphonuclear leucocytes, monocytes/macrophages and dendritic cells. To distinguish this cell type from hematopoietic cells of somatic cell origin, we will refer to this new cell type as a "multipotent lymphohematopoietic progenitor."

In one embodiment, the present invention is a cell culture comprising a purified population of multipotent lymphohematopoietic progenitor cells which are derived from human embryonic stem cells and exhibit the cell surface markers CD34+, CD43+, CD45− and are Lin−. Preferably, the multipotent lymphohematopoietic progenitor cells are at least 90%, most preferably at least 95%, of a cell population.

CD34+CD43+CD45− cells are at least 0.3-0.6% of total cell population in hESC/OP9 coculture or 4% of CD34+ cells or 20% of CD43+ cells. When we purify CD34+CD43+ CD45− cells they are typically more than 95% pure.

By "purified", we mean that the cell population has been subject to some selection process so that the population is richer in multipotent lymphohematopoietic progenitor cells than the population before purification. For example, the step of selecting for CD43+ subsets of cells by MACS (magnet-activated cell sorter) selection followed by FACS (fluorescence-activated cell sorter) sorting, as described below in Example 1, is a "purification".

The optimal hematopoietic precursor or progenitor cell will not have committed to any of its derivative blood cell lineages as of yet, since it retains the capability to differentiate into any of them This characteristic is monitored by looking for the absence of cell surface markers indicative of differentiation into any of the derivative lineages. This trait is summarized as referring to the cells as "Lin⁻", an abbreviation for lineage minus, which means that the preferred multipotent lymphohematopoietic progenitor cells of the present invention are CD41a−, CD235a−, CD3−, CD19−, CD11b−, CD14− and HLA-DR−, thus lacking all of the indicators of the progeny lineages. The novel multipotent lymphohematopoietic lineage of the present invention is thus characteristically CD34+CD43+Lin⁻ and CD45−.

The lymphohematopoietic progenitors described here typically have the gene profile characteristics of Flt-1+, KDR+, Flt-3$^{low}$, GATA-3$^{high}$, RUNX1$^{high}$ and MPO (myeloperoxidase)−. This gene expression profile is characteristic for the primitive hematopoietic progenitors which possess stem cell potential which have been found in human embryo (Tavian M, et al., Ann N Y Acad. Sci. 2005 June; 1044:41-50). The CD34+CD43+Lin⁻CD45− cells are capable of differentiation into the B and NK lymphocytes, myeloid cells, erythroid cells, and megakaryocytes. If continued in culture, these cells will later acquire the marker CD45. However, ES-derived CD45+ cells lack potential to form B lymphoid cells and have a tendency to differentiate into myeloid cells. The CD45+ cells have a gene expression profile of Flt-1−, KDR−, Flt-3$^{high}$, GATA-3$^{low}$, RUNX1$^{low}$ and MPO+, which is an expression profile of more mature progenitors, which have lost some of the potency of the earlier progenitors.

In another embodiment of the invention, one would wish to isolate myeloid progenitors generated from hESC in OP9 coculture which are CD34+CD43+CD45+Lin⁻ with greater than 95% purity.

In another embodiment of the invention, one would wish to isolate erythromegakaryocytic progenitors generated from hESC in OP9 coculture, which are CD34±CD43+CD235a+CD41a+. The purity of these progenitors is typically greater than 95%.

All cell subsets arise in hESC/OP9 coculture as described below. CD43+CD45+ cells are derived from CD43+CD45−, but one does not have to isolate and culture CD43+CD45− cells to obtain CD43+CD45+ cells.

In another embodiment, the present invention is a population of B cells, NK cells or myeloid cells derived from the lymphohematopoietic precursor cells of the present invention.

Method of Creating a Population of Multipotent Lymphohematopoietic Progenitor Cells In another embodiment, the present invention is a method for generating a population of multipotent lymphohematopoietic progenitor cells. To make the lymphohematopoietic cells of the present invention, one begins with human ES cells and cultures the cells under conditions which favor differentiation into the hematopoietic lineage.

There are several techniques which can induce human ES cells to differentiate into the hematopoietic lineage. In the Examples below, we use co-culture with stromal cells, a previously described technique to induce hematopoietic differentiation as taught, for example, in U.S. Pat. No. 6,280,718, the disclosure of which is hereby incorporated by reference. It is believed that any other methodology for the generation of hematopoietic progenitors from ES cells will follow a similar pattern and proceed through a CD45− stage of multipotency before becoming CD45+ and losing lymphoid potential.

The co-culture system exemplified here is based on a macrophage colony-stimulating factor (M-CSF) deficient stromal cell line, such as the murine line OP9, which fosters the differentiation of human ES cells into hematopoietic cells. During the co-culture, the first hematopoietic colony forming cells (CFCs) were detectable 1 day after emergence of CD34+ cells, which was approximately day 4 or 5 of the culture and 2 to 3 days before the generation of CD45+ cells. The timeline of the emergence of the cell surface markers is illustrated in FIG. 9.

Positive selection of CD43+ from the cells which were also CD34+ resulted in total recovery of all types of CFCs from the culture. Cells which are true multipotent hematopoietic precursors can generate colony forming units (CFUs) or colony forming cells (CFCs). The literature is not uniform in the characterization of the types of these units or cells. For purposes of this discussion, the types of CFC generated were characterized as E-CFC (erythroid CFC), GEMM-CFC (granulocyte/erythroid/macrophage/megakaryocyte CFC), GM-CFC (granulocyte/macrophage CFC) and M-CFC (megakaryocyte CFC). In addition, E-CFCs, which were consistently detected in the CD34− fraction, were also recovered by CD43+ selection. We concluded that CD43 is the first pan-hematopoietic marker detectable on human ES cell derived hematopoietic precursors and can thus be used to for separation of CD34+ hematopoietic progenitors.

We have found that this separation can be useful because the CD34+CD43− can be subdivided into two populations, one which is KDR+ and one which is KDR−. The phenotype of CD34+CD43−KDR+ seemed to be dedicated to an epithelial lineage. Only cells which had become CD34+ and CD43+ were committed to the hematopoietic lineage.

Thus, we propose that all hematopoietic progenitors generated by co-culture of human ES cells with stromal cells can be identified by expression of CD34 and CD43. The first CD43+ cells are CD45− and a large proportion of these cells co-express CD41a and CD235a. Later the expression of CD45 arises. The population of CD43+CD45− cells lack CD41a, CD235a and other lineage-restricted markers and represent CD34+CD43+CD45− multipotent lymphohematopoietic progenitors. By the time the cells express CD45, they lose the ability to differentiate into lymphoid cells, as indicated by our inability to recover B cells from these progenitors cells. The preferred cell population is the cells which are CD34+, CD43+ and, in addition, are CD45− and Lin⁻.

Factors that we believe are useful in hESC differentiation with OP9 cells are:

1. OP9 cells have recently been characterized as a preadipocyte cell line. In fact, many researchers mention the massive adipogenesis in OP9 cultures shortly after confluence. OP9 cells used in our laboratory exhibit diminished adipogenic properties, possibly due to continuous subculture on the gelatin-coated plastic, that we initially found to be important for selection of highly inductive OP9 cells. (One typically measures adipogenic potential by viewing the cells under a microscope. Preferred cell populations of the present invention present only a few cells with lipid-containing vacuoles, as observed under a microscope.) These cells, however, retain adipogenic potential since adipogenic differentiation can be induced by short-term culture in serum-free media. Less adipogenic OP9 cells more easily allow us to obtain the high-density overgrown OP9 cultures, which are critical for efficient generation of hematopoietic progenitors in hESC/OP9 cocultures.

Adipogenic potential of OP9 cells means ability of stromal cells to differentiate into adipocytes. Adipocytes are recognized and under the microscope as a cells accumulated lipid-containing vacuoles. Culture conditions which results in formation of cell monolayer containing a lot of adipocytes are considered adipogenic.

2. Basal α-MEM medium is essential for OP9 cells. Freshly prepared α-MEM from powder formulation is more suitable than liquid commercial medium. We did not find an advantage of α-MEM formula supplemented with nucleosides for hematopoietic differentiation in hESC/OP9 cocultures, although this medium significantly increases proliferation of OP9 cells. One peculiarity of α-MEM formula is a high concentration of ascorbic acid (50 μg/ml). We found that additional supplementation of hESC differentiation medium (α-MEM-based medium for hESC/OP9 cocultures) with 50 μg/ml ascorbic acid increases the yield of CD34+ and CD43+ cells and may be recommended for poorly differentiating hESC lines.

3. Use of SH-agents (sulfhydryl) in hESC differentiation medium is optional. Differentiation proceeds efficiently without addition of any SH-agents. However, the yield of total cells in MTG (monothioglycerol)-supplemented cultures is consistently higher, suggesting a favorable effect of SH-agents on cell survival and growth during differentiation. We found that 2-ME (Mercaptoethanol) is suppressive for differentiation starting from 50 μM concentration, while MTG is permissive for up to 200 μM. We propose 100 μM MTG concentration as optimal for differentiation medium. Addition of MTG to GM-CSF expansion cultures may delay emergence of proliferating myeloid cells. However its presence is essential for long-lasting growth of myeloid progenitors.

4. Semiconfluent MEF (mouse embryonic fibroblasts) monolayers are optimal for hESCs culture. Over-crowding MEFs suppress growth of hESC colonies and may stimulate their spontaneous differentiation. MEFs from different batches and prepared using different lots of plastic and FBS may vary in cell size. Therefore, MEF plating density should be adjusted accordingly to ensure semiconfluent feeder layers for hESC subculture. "Monolayer" is a layer of cells wherein the layer is one cell thick. "Confluent" means the layers of cells are merging together. "Semiconfluent" means that the monolayer of cells does not reach confluence. Therefore, the cells do not merge together and there is distance between the cells.

5. After treatment of hESC cultures with collagenase, nearly all hESC colonies should be dislodged easily by washing or very gentle scraping. Intensive scraping should be avoided to prevent excessive mechanical damage to cells and collection of the firmly attached colonies, which may contain differentiated cell types.

6. During OP9 maintenance, cultures should be split no later than next day after confluence. Because OP9 growth is largely influenced by FBS, a split ratio must be adjusted with each new lot of FBS. The same type of FBS is usually used for OP9 maintenance and differentiation in hESC/OP9 cocultures. We select FBS lots with minimal adipogenic effect on confluent OP9 cells after feeding with ½ volume of fresh medium and prolonged culture for 4-6 days. We found that different lots of HyClone "defined" FBS (without heat inactivation) support efficient OP9 growth with minimal if detectable adipogenesis in overgrown OP9 cultures and also provide a relatively stable hematopoietic differentiation in hESC/OP9 cocultures. Results with FBS from other suppliers were more variable, yet not systematically studied.

7. Optimal plating density of hESCs in OP9 cocultures may vary for different hESC lines. It is primarily dependent on intensity of hESC growth: hESC lines with a higher proliferation rate in undifferentiated cultures may require a lower plating density in OP9 cocultures. The density of the $1.5-2\times10^6$ cells/OP9 dish is optimal for H1 cells, though H9 cells differentiate more efficiently starting from a lower density ($1-1.5\times10^6$ cells/OP9 dish). Optimal plating density for other hESC lines should be established in preliminary experiments using an initial range of $0.5-2.5\times10^6$ cells/OP9 dish with 0.5 intervals.

8. hESC/OP9 cocultures on day 9-10 of differentiation may form a matrix that withstands digestion with collagenase and trypsin. As a result, many cells may be lost due to clumping and mechanical damage during pipetting. Longer incubations with collagenase and trypsin (up to 30 min each) should be tried first to improve cell recovery. In addition, supplementation of collagenase solution with 0.1 mg/ml hyalouronidase IV-S (Sigma; cat. no. H3884) can be further used to improve dissociation of hESC/OP9 monolyers.

Method of Creating a Population of B Cells, NK Cells or Myloid Cells

In another embodiment, the present invention is a method of deriving various cell types from the multipotent lymphohematopoietic progenitors described above. Example 2, below, shows preferred methods.

In general, one would first generate a population of lymphohematopoietic cells, preferably comprising the steps of culturing human embryonic stem cells under conditions which favor differentiation of the cells into the hematopoietic lineage and isolating from the culture cells which have the lymphohematopoietic characteristics of exhibiting the cell surface markers CD34+, CD43+ and CD 45−. Preferably, the cells are Lin⁻. One would then culture CD34+ cells which comprise 10-20% CD34+CD43+ of hematopoietic progenitors, up to 60% of endothelial cells and less than 15% of CD34+CD43−KDR− mesenchymal cells or isolated CD34+CD43+CD45− Lin⁻ cells on MS-5 stromal cells under conditions that favor lymphocyte development (αMEM containing 10% of FBS, 100 μM MTG, SCF 50 ng/ml, Flt-3L 50 ng/ml, IL-7 20 ng/ml, IL-3 5 ng/ml) with the media change every 4$^{th}$ day. After 4-6 weeks of culture approximately 2% of cells express B-lymphocyte marker CD19 and more than 15% of cells are immature CD45+ CD56+ NK cells. Treatment of immature NK cells with 20 ng/ml of IL-15 induces their maturation into perforin-positive cytolytic NK cells.

One would then culture CD34+ cells which compromised 10-20% CD34+CD43+ of hematopoietic progenitors, up to 60% of endothelial cells and less than 15% of CD34+CD43− KDR− mesenchymal cells or isolated CD34+CD43+CD45− Lin⁻ or CD34+CD43+CD45+Lin⁻ cells on MS-5 stromal cells under conditions that favor myeloid development (αMEM containing 10% of FBS, 100 μM MTG, SCF 50 ng/ml, G-CSF 20 ng/ml, GM-SCF 10 ng/ml, IL-3 10 ng/ml) with media change every 4$^{th}$ day. After 21 days myeloid cells, including polymorphonuclear leukocytes and cells of monocyte/macrophage/denritic cell lineage, develop.

Both CD34+CD43+CD45− Lin− and CD34+CD43+ CD45+Lin− precursors also produce megakaryocytes. These cells can also be used to obtain T cells.

Use of Multipotent Lymphohematopoietic Progenitor Cells

In another embodiment, the present invention is the use of a population of multipotent lymphohematopoietic progenitor cells, or other cell populations of the present invention, in toxicity tests for various substances.

In one embodiment, one would expose the substance to a population of cells of the present invention and evaluate the effect of the substance on further cell differentiation. For example, one would expose a test compound to the multipotent lymphohematopoietic progenitor cell population and then determine, in contrast to a control population that has not been exposed to the compound, whether the cells maintain their ability to further differentiate into B cells, NK cells or myeloid cells.

In vivo substances such as anticancer drugs, xenobiotics, microbial toxins and ionizing radiation destroy rapidly dividing marrow progenitors and single exposure may result in acute, reversible neutropenia, thrombocytopenia and possibly anemia and lymphocytopenia. Important goals during preclinical drug development are to predict whether a new agent will be clinically toxic to the bone marrow, whether toxicity will be specific to one or more cell lineage (lymphocytes, neutrophils, megakaryocytes, or erythrocytes), and at what dose or plasma level the drug will be toxic. Myelotoxicity is one of the major limitations to the use of full doses of antitumor agents, and the goal of the regulatory setting is the prediction of the highest dose that will not cause clinically adverse effects and the dose that causes maximally tolerated, reversible perturbations in peripheral blood count. In vitro tests can be used to refine safety margins by reducing toxicological uncertainties due to human extrapolations and provide a rational basis for calculating clinical dosages and for setting exposure limits. HESC-derived hematopoietic progenitors can be used as alternative to a somatic (bone marrow or cord blood) source of cells for drug toxicity screening.

All CD34+CD43+CD45− Lin− cells, CD34+CD43+ CD45+Lin−, and CD34+CD43+CD41+CD235a+ cells can be used for toxicity screening. CD34+CD43+CD45− Lin− preferentially can be used for drug toxicity testing on lymphocytes and multipotent GEMM-progenitors, CD34+ CD43+CD45+Lin− cells preferentially can be used for testing myelotoxicity, and CD34+CD43+CD41+CD235a+ can be used for testing drugs affecting RBC production.

A prophetic protocol for evaluation of the potential hematotoxicity of anticancer drug from their direct effect on colony forming cells follows:

To induce hematopoietic differentiation hESC cells are cultured with OP9 stromal cells for 8 days as described below. CD43+ cells or CD43+CD45−Lin− or CD43+CD45+ Lin− cells are isolated using MACS and FACS cell sorting as described below. To 10 tubes containing 3 ml of Metho-Cult GF+ semisolid medium are added 0.2 ml of cells diluted with IMDM media containing 2% of FBS. The recommended final concentrations of cells are: CD43+1000 cells/ml, CD43+CD45−lin− cells 400 cells/ml, CD43+ CD45+ lin− 200 cells/ml.

To each tube containing semisolid medium with cells are added 100 µl of IMDM (control tube 1), 75 µl of IMDM plus 25 µl of vehicle (D0 tube, vehicle control) and 75 µl of IMDM plus 25 µl of ten-fold anticancer drug dilution to (D1-D9 tubes). Drugs are diluted to achieve the final fold concentrations of drug in the culture dish of $10^{-2}$, $10^{-3}$, $10^{-4}$, $10^{-5}$, $10^{-6}$, $10^{-7}$, $10^{-8}$, $10^{-9}$. Mixtures are dispensed to a 35 mm pre-tested culture dish (StemCell Techologies) in duplicate and incubated for 14 days in 5% CO2 under saturated humidity.

The colonies are counted under the microscope. The first drug dilution that completely inhibits CFU and last drug dilution that does not inhibit CFU are identified to calculate concentrations that inhibit CFU by 50% and 90% (IC50 and IC90). IC50 and IC90 can be used as predictive points for maximal tolerated dose of drugs (Pessina A, et al., *Toxicol Sci.* 2003 October; 75(2):355-67).

EXAMPLES

The Examples below are based on Vodyanik, et al., *Blood*, 108(6) 2095-2105, September 2006, pre-published online Jun. 6, 2006 DOI 10.1182/blood-2006-02-003327 and Vodyanik, et al., *Blood*, 105(2) 619-628, January 2005, both incorporated by reference.

1. Leukosialin (CD43) Defines Hematopoietic Progenitors in Human Embryonic Stem Cell Differentiation Cultures A. Materials and Methods Cell Lines H1 and H9 hESC lines (Thomson J A, et al., *Science* 1998; 282:1145-1147) were obtained from WiCell Research Institute (Madison, Wis.), and maintained in an undifferentiated state by weekly passages on mouse embryonic fibroblasts as described. (Amit M, et al., *Developmental Biology* 2000; 227:271-278.) Mouse OP9 stromal cell line was kindly provided by Dr. Nakano (Osaka University, Japan). OP9 was maintained on gelatin-coated plastic in αMEM (GIBCO-Invitrogen, Carlsbad, Calif.) supplemented with 20% defined FBS (HyClone Laboratories, Logan, Utah). Mouse MS-5 stromal cell line was obtained from DSMZ GmbH (Braunschweig, Germany), and maintained in αMEM supplemented with 5% heat-inactivated FBS (GIBCO).

hESC Differentiation in OP9 Coculture

Hematoendothelial hESC differentiation in OP9 coculture was performed as previously described. (Vodyanik M A, Bork J A, Thomson J A, Slukvin, I I. Human embryonic stem cell-derived CD34+ cells: efficient production in the coculture with OP9 stromal cells and analysis of lymphohematopoietic potential. Blood. 2005; 105:617-626.) Briefly, overgrown OP9 cultures were prepared by feeding and prolonged culture of confluent OP9 cells for 4 days. hESCs prepared in suspension of small cell aggregates were added to OP9 cells in αMEM supplemented with 10% FBS (HyClone) and 100 µM monothioglycerol (MTG; Sigma, St. Louis, Mo.). hESC/OP9 cocultures were incubated up to 9 days in standard conditions (37° C., 5% $CO_2$, >95% humidity). Half of the medium was replaced with fresh medium on days 4, 6, and 8. For cell harvesting, hESC/OP9 monolayers were dispersed by successive enzymatic treatment with collagenase IV (GIBCO; 1 mg/ml) for 20 minutes at 37° C., and 0.05% trypsin-0.5 mM EDTA (GIBCO) for 15 minutes at 37° C. Cells were resuspended by pipetting, washed twice in PBS-5% FBS, filtered through a 70 µM cell strainer (BD Falcon, Bedford, Mass.) and used for further analysis and cell sorting.

Cell Sorting

Isolation of $CD34^+$ cells and subsequent separation of $CD34^+CD43^+$ and $CD34^+KDR^{+/-}$ subpopulations was performed by multi-parameter magnet-activated cell sorting (MACS) using MicroBeads, MidiMACS magnet and LS+ columns from Miltenyi Biotech (Bergisch Gladbach, Germany). A single-cell suspension from hESC/OP9 cocultures was incubated with basic (non-conjugated) MicroBeads, washed with PBS-5% FBS, and passed through MidiMACS/LS+ unit to remove cells that bind the beads/column non-specifically. CD34+ cells were isolated using CD34 Multisort MicroBeads and further processed to remove the Ab-tagged magnetic label as recommended by the manufacturer. Isolated CD34+ cells were stained with CD43-FITC and KDR-PE mAbs. The CD34+CD43+ subpopulation was isolated by anti-FITC MicroBeads, and CD43-negative fraction was separated into CD34+CD43−KDR+ and CD34+CD43−KDR− subpopulations by anti-PE MicroBeads. In some experiments, CD43+ cells were directly isolated using CD43 MicroBeads. As determined by fluorescence-activated cell sorter (FACS) analysis, purity of MACS-isolated CD34+ subpopulations was >95%.

For sorting of CD43+ subsets, total CD43+ cells were isolated from hESC/OP9 cocultures by positive MACS selection using CD43-FITC mAb/anti-FITC MicroBeads labeling. MACS-enriched CD43+ cells were stained with CD41a-PE, CD235a-PE and CD45-APC mAbs, and CD43+ subsets (CD43+CD41a/CD235a+CD45−, CD43+CD41a/CD235a−CD45−, CD43+CD41a/CD235a−CD45+) were separated on a FACSVantage cell sorter (BDIS, San Jose, Calif.) using cell gating by scatter parameters (live cells) and positive FITC staining (total CD43+ cells). Purity of sorted fractions as verified by FACS analysis was >98%.

FACS Analysis

For cell surface staining, cells were prepared in PBS-2% FBS containing 0.05% sodium azide, 1 mM EDTA and 1% mouse serum (Sigma), and labeled with multicolor mAb combinations. For intracellular staining, cells were fixed and permeabilized using Fix&Perm reagents (Caltag-Invitrogen). Samples were analyzed using FACSCalibur flow cytometer (BDIS) and FlowJo software (Tree Star, Inc., Ashland, Oreg.) as previously described (Vodyanik M A, et al., Blood 2005; 105:617-626). All mAbs used in this study (supplemental Table S1) were verified for non-reactivity with OP9 cells.

Endothelial Cell Culture and Assays

To reveal endothelial cells in CD34+ subpopulations, cells were plated onto gelatin-coated 6-well plates at $2 \times 10^5$ cells/well in 3 ml complete medium containing endothelial serum-free medium (ESFM; GIBCO) supplemented with 5% FBS (GIBCO), 20 ng/ml basic fibroblast growth factor (FGF; Invitrogen) and 1/100 dilution of endothelial cell growth factor (acidic FGF+heparin; Sigma). Endothelial cells were further expanded on fibronectin-coated dishes in complete medium without FBS. In some experiments, endothelial cultures were treated overnight with 25 ng/ml tumor necrosis factor (TNF; Peprotech, Rocky Hill, N.J.) and examined for ICAM-1/VCAM-1 expression by flow cytometry. For immunofluorescent staining, endothelial cultures were prepared on fibronectin-coated chamber glass slides (BD Falcon), fixed with 4% paraformaldehyde, permeabilized with 0.1% Triton X-100 and blocked with Image-iT-FX signal enhancer (Molecular Probes-Invitrogen). Slides were stained with indicated antibodies and examined on a DMIRB fluorescent microscope (Leica Microsystems Inc., Bannockburn, Ill.) equipped with MagnaFire camera/software (Optronics, Goleta, Calif.).

For acetylated low-density lipoprotein (Ac-LDL) uptake assay, endothelial cultures were incubated with 10 µg/ml DiI-Ac-LDL conjugate (Biomedical Technologies Inc., Stoughton, Mass.) for 4 hours at 37° C., washed three times with PBS (with Ca/Mg), and inspected under fluorescent microscope or dispersed and analyzed by FACS to determine % of Ac-LDL-incorporating cells. Parallel cultures incubated at 4° C. were used as a control.

For vascular tube formation, growth factor reduced Matrigel (BD Falcon) was added into a 24-well plate (0.5 ml/well) and allowed to solidify for 1 hour at 37° C. Cells prepared in ESFM with 40 ng/ml VEGF$_{165}$ (Peprotech) were plated onto a gel matrix ($5 \times 10^4$ cells/well in 0.5 ml medium) and incubated 12 hours at 37° C.

Hematopoietic Colony-Forming Assays and Lymphomyeloid Cultures

Hematopoietic clonogenic assays were performed using MethoCult GF+ complete methylcellulose medium with FBS and cytokines (SCF, G-CSF, GM-CSF, IL-3, IL-6, EPO) and MegaCult serum-free collagen assay with cytokines (TPO, IL-3, IL-6) (Stem Cell Technologies, Vancouver, Canada). MegaCult medium formulated for detection of megakaryocytic (Mk) colony-forming cells (CFC) was additionally supplemented with 75 ng/ml SCF (Peprotech) and 5 units/ml erythropoietin (Stem Cell Technologies) to enable simultaneous detection of erythroid CFCs. Cell plating densities for CFC assays were optimized according to day of hESC differentiation or cell subsets tested (supplemental Table S2). Colonies were scored after 14-21 days of incubation according to morphological criteria as erythroid (E), granulocyte/macrophage (GM), macrophage (M), and mixed (Mix) colonies containing erythroid and non-erythroid cells. Multilineage mix-colonies were identified as large, often irregular, multicentric colonies containing myeloid (Granulocytes and Macrophages) and Erythro-Megakaryocytic component (GEMM). Identification of Mk-colonies in collagen gels was performed by CD41a immunostaining according to protocol supplied with MegaCult kit.

For lymphoid and myeloid differentiation, CD43+ subsets were seeded on irradiated (50 Gy) MS-5 stromal monolayers at density of $10^3$ cells/well of 6-well plates in 4 ml complete αMEM containing 10% FBS (HyClone), 100 µM MTG and either myeloid (SCF, 50 ng/ml; G-CSF, 20 ng/ml; IL-3, 10 ng/ml) or lymphoid (SCF, 50 ng/ml; Flt-3L, 50 ng/ml; IL-7, 20 ng/ml; IL-3, 5 ng/ml) cytokine combinations (all cytokines were from Peprotech). Every 4 days, the plates were gently agitated and half of the medium containing non-adherent cells was replaced with fresh complete medium without IL-3. In indicated time-points, non-adherent cells were collected and adherent cells were dispersed as described above for hESC/OP9 cocultures. Non-adherent and adherent cells were pooled and assayed for myeloid CFCs by MethoCult assay, total CD43+ cells by FACS and lymphoid transcripts by RT-PCR.

Gene Expression Analysis by RT-PCR

Total RNA from hESCs, stromal cells and cocultures was isolated with RNAwiz (Ambion, Austin, Tex.). Total RNA from sorted cell fractions was isolated using Perfect RNA Eukaryotic mini isolation kit (Eppendorf, Hamburg, Germany). All RNA samples were treated with DNAse using DNAfree reagents (Ambion). cDNA was prepared from 1 µg total RNA by oligo-dT$_{15}$-primed reverse transcription (RT) with StrataScript RT kit (Stratagene, La Jolla, Calif.). Quantitative PCR (qPCR) was performed using Brilliant SYBR Green QPCR master mix (Stratagene). Real-time PCR detection was performed on ABI Prism 7700 Sequence Detection System (Applied Biosystems, Foster City, Calif.) and the mean minimal cycle threshold values (Ct) from duplicate reactions were derived. All qPCR products were analyzed on 2% agarose gels to confirm the specificity of detection. Quantification of target genes was Performed in comparison to the reference GAPDH gene as described (Pfaffl MW. A new mathematical model for relative quantification in real-time RT-PCR. Nucleic Acids Res. 2001;

29:2002-2007) and expressed as a ratio (R; fold differences to GAPDH). GAPDH was used as a reference gene because its expression remains constant during ESC differentiation. (Murphy C L, et al., Tissue Eng. 2002; 8:551-559.) Relative expression in the group of n samples to be compared was calculated as Rn/ΣR(n) (contribution of each R value to the pooled R values across the group).

B. Results

CD43 is the Earliest and Predominant Pan-Hematopoietic Marker Expressed by Differentiating hESCs in OP9 Coculture We have previously demonstrated that early hematopoietic progenitors generated in hESC/OP9 coculture arise within CD34$^+$ cell population; however, CD34$^+$ cells are heterogeneous and include at least endothelial cells (Vodyanik M A, et al., Blood 2005; 105:617-626). To define the earliest and specific marker for hematopoietic progenitors, we analyzed expression of CD45, CD43, CD41a (GPIIb) and CD235a (glycophorin A) during hESC/OP9 coculture. In humans, both CD45 and CD43 are considered as pan-hematopoietic markers, (Remold-O'Donnell E, et al., Blood 1987; 70:104-109; Dahlke M H, et al., Leuk Lymphoma 2004; 45:229-236) though CD45 is not expressed on platelets and cells of the erythroid lineage, (Dahlke M H, et al., Leuk Lymphoma 2004; 45:229-236) while CD43 is expressed on platelets and erythroid progenitors, but it is not detected on mature erythrocytes and B-cell subsets. (Remold-O'Donnell E, et al., Blood 1987; 70:104-109; Wiken M, et al., Scand J Immunol. 1988; 28:457-464) CD41a and CD235a are known markers of megakaryocytic and erythroid cell lineages, respectively (Phillips D R, et al., Blood 1988; 71:831-843; Loken M R, et al., Blood 1987; 70:1959-1961).

Using PCR and flow cytometry, we found that undifferentiated hESCs did not express CD235a and CD45 mRNA (FIG. 1A) or protein (not shown). While CD34, CD43 and CD41a mRNAs were detected in undifferentiated hESCs (FIG. 1A), no surface or intracellular expression of these proteins was detected by flow cytometry (not shown).

Figure 1B:
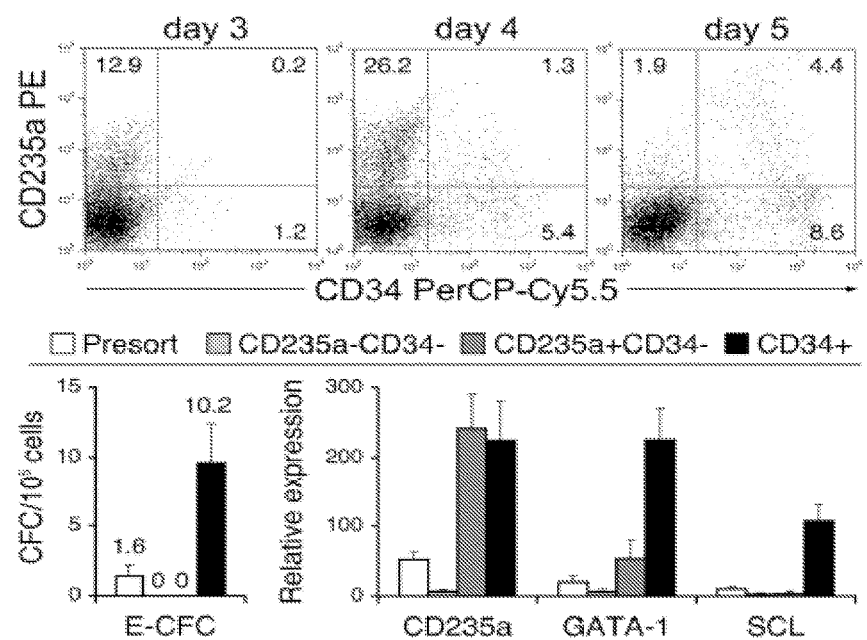
FIG. 1. Kinetic analysis of hematopoietic development in H1/OP9 coculture. (A) Gene expression analysis of hematopoiesis-inductive transcription factors (SCL, GATA-1) and hematoendothelial markers by RT-PCR. Triangular white pointers indicate the first day when a surface expression of respective hematopoietic markers was detected by flow cytometry. Dotted vertical lines show the timeframe of CFC emergence. Human- and mouse-specific GAPDH primers were used for positive control of human (hGAPDH) and MEF/OP9 (mGAPDH) RNA, respectively. (B) Early CD235a$^+$CD34$^-$ cells in H1/OP9 coculture. Representative FACS analysis shows a burst-like CD235a expression and gradual emergence of CD34$^+$CD235a$^{+/-}$ cells during 3-5 days of H1/OP9 coculture. Values within dot-plots indicate % of cells in respective quadrants; 20000 FACS events are displayed. Bar graphs show CFC potential and relative expression of CD235a, GATA-1 and SCL mRNA in FACS-sorted CD235a$^-$CD34$^-$, CD235a$^+$CD34$^-$ and CD34$^+$ cells on day 4 of H1/OP9 coculture. CFCs and mRNA levels were determined by MethoCult GF+ assay and qRT-PCR, respectively. The relative expression of each GAPDH-normalized target gene was calculated in comparison with undifferentiated H1 cells using the $2^{-\Delta\Delta Ct}$ method. Results are the mean±SD from 3 independent experiments. (C) Expression of hematopoietic markers during H1/OP9 coculture was analyzed by FACS within gated CD34$^+$ cells, and represented as a percentage of CD34$^+$ cells (left Y-axis). Dashed trend line shows total CFC counts (right Y-axis). Results are the means from 3 independent experiments. (D) Representative FACS analysis of CD43$^+$ cells in H1/OP9 coculture. Values within dot-plots indicate % of cells in respective quadrants; 20000 (total H1/OP9 cells), 5000 (gated CD34$^+$ cells, day 5) and 10000 (gated CD34$^+$ cells, days 7, 9) FACS events are displayed.

The first hematopoietic marker detected in hESC/OP9 coculture was CD235a. CD235a$^+$ cells emerged abruptly in relatively high numbers on day 3 of differentiation (FIG. 1B) coincidentally with up-regulation of CD34 and CD43 mRNA, and induction of SCL and up-regulation of GATA-1 transcription factors (FIG. 1A), which are known primary inducers of hematopoietic commitment (Keller G., Genes Dev. 2005; 19:1129-1155; Fujimoto T, et al., Genes Cells 2001; 6:1113-1127; Orkin S H, Int J Dev Biol. 1998; 42:927-934). However, almost all day 3 CD235a$^+$ cells were CD34$^-$, and only a few CD34$^+$CD235a$^{+/-}$ cells could be detected by flow cytometry (FIG. 1B). Both CD235a$^+$CD34$^-$ and CD34$^+$ cells continued to increase on day 4, while a significant drop in CD235a$^+$CD34$^-$ and a rise in CD34$^+$CD235a$^+$ cells were observed on day 5. Comparative analysis of isolated CD235a$^+$CD34$^-$ and CD34$^+$ cells revealed that SCL and GATA-1 were predominantly expressed in CD34$^+$ cells and only CD34$^+$ cells contained E-CFCs (first-detectable on day 4, FIG. 1B). Moreover, CD235a$^+$CD34$^-$ cells demonstrated morphologic heterogeneity and were lacking typical erythroblastoid cells. Thus, these results confirm our previous observation that first hESC-derived hematopoietic progenitors are confined to CD34$^+$ cells.

Figure 1D:
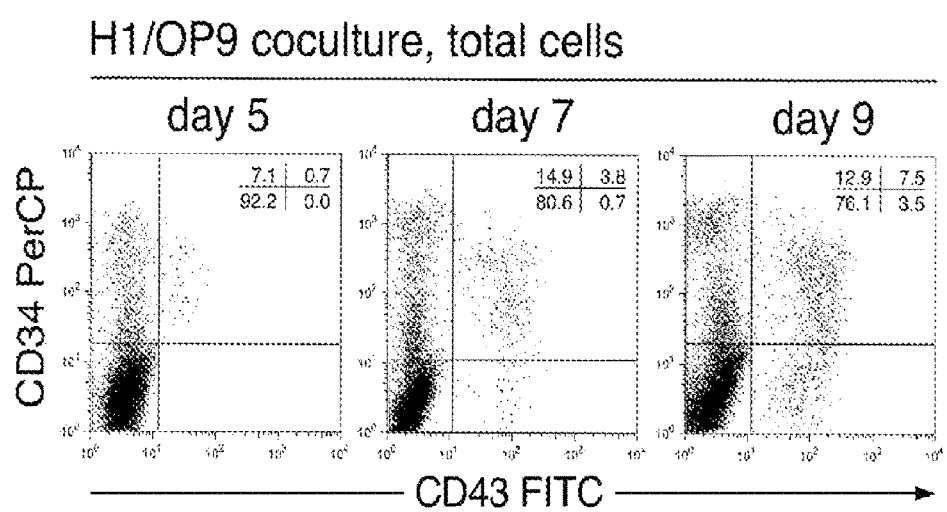
Figure 1D:
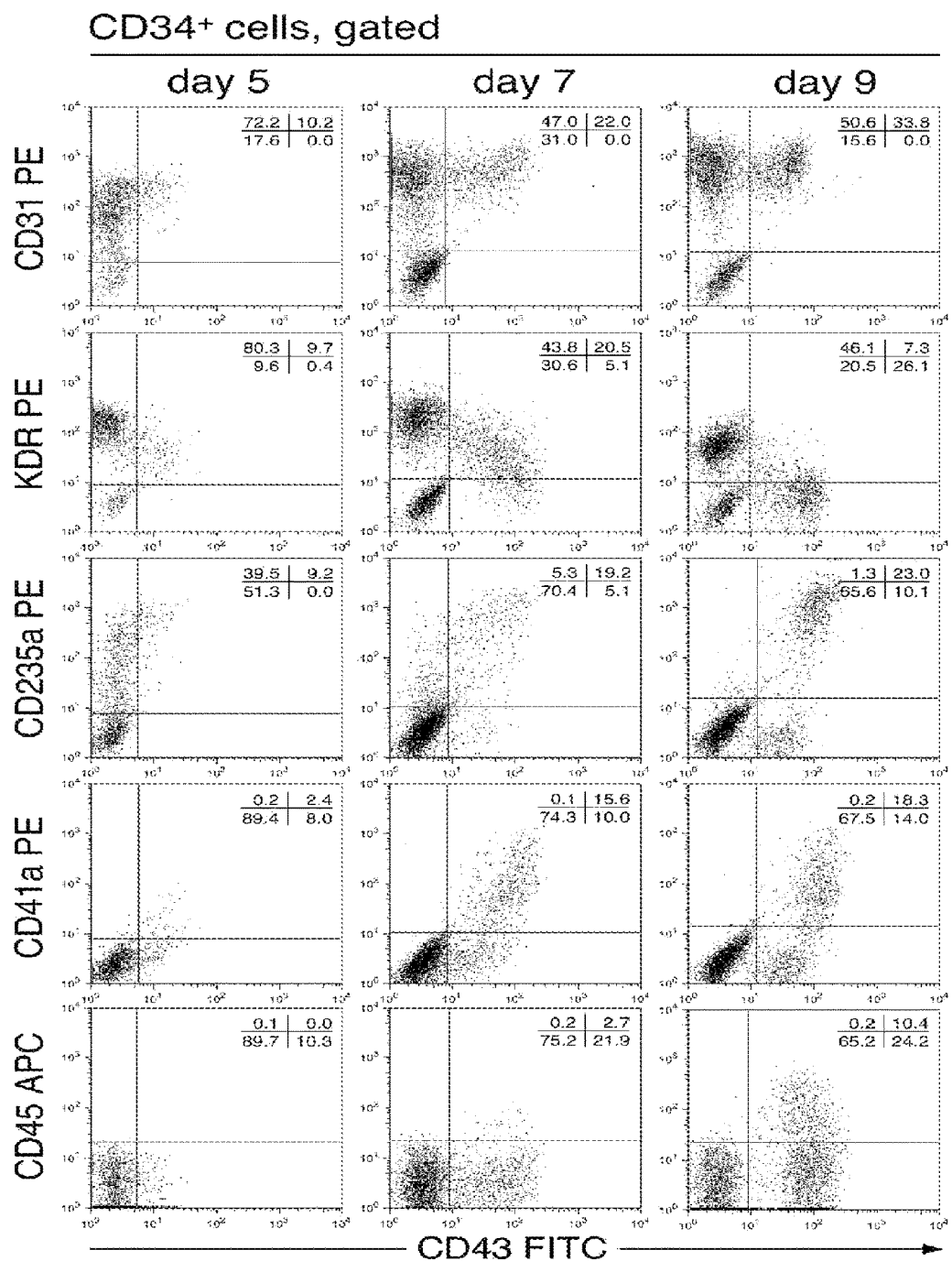

The first CD43$^+$ cells were detected on day 4-5 of differentiation as subpopulation of CD34$^+$ cells expressing the highest density of CD235a (FIG. 1C, D). Their emergence strictly correlated with the appearance of the first E-CFCs. The first CD41a$^+$ and CD45$^+$ cells were detected as subpopulations of CD43$^+$ cells on day 5 and day 7, respectively. On day 9, almost all CD235a$^+$, CD41a$^+$ and CD45$^+$ cells were found within a more numerous CD43$^+$ population (FIG. 1C, D). Notably, early CD43$^+$ cells expressed endothelial markers KDR (VEGF-R2) and CD31 (PECAM-1). KDR was down-regulated on CD43$^+$ cells along with advanced differentiation, whereas CD31 was stably expressed (FIG. 1D).

To reveal hematopoietic markers expressed by clonogenic progenitors, we evaluated the CFC potential of cells from hESC/OP9 coculture after depletion of CD34$^+$, CD43$^+$, CD235a$^+$, CD41a$^+$ and CD45$^+$ cells. As shown in Table 1, only depletion of CD43$^+$ cells resulted in complete removal of all CFC types throughout hESC/OP9 coculture. CD34$^+$ depletion led to complete removal of the Mix/GM/M-CFCs, whereas E-CFCs were progressively detected in CD34$^-$ fractions after 6 days of hESC/OP9 coculture. These results indicated that erythroid progenitors down-regulated CD34 expression with advanced maturation, but retained CD43 expression. Separation of CD41a$^+$, CD235a$^+$ and CD45$^+$ cells resulted in partial, mostly erythroid (CD41a, CD235a) or myeloid (CD45) CFC depletion.

These data demonstrate that CD43 is a pan-hematopoietic marker of the earliest clonogenic progenitors and differentiating hematopoietic cells, and can be used for selection of the entire hematopoietic population generated in hESC/OP9 coculture.

TABLE 1

CFC depletion by antibodies against hematopoietic markers

| Depleted cell subset | Day of differentiation | CFC depletion, % | | | |
|---|---|---|---|---|---|
| | | E-CFC | Mix-CFC | GM-CFC | M-CFC |
| CD34$^+$ | 5 | 100 | NA | NA | NA |
| | 6 | 96.8 ± 2.6 | 100 | 100 | 94.2 ± 11.6 |
| | 7 | 62.3 ± 16.2 | 98.0 ± 3.5 | 97.7 ± 4.1 | 96.1 ± 3.6 |
| | 8 | 37.8 ± 17.3 | 99.6 ± 0.8 | 99.1 ± 3.5 | 99.4 ± 2.3 |
| CD43$^+$ | 5 | 98.3 ± 3.3 | NA | NA | NA |
| | 6 | 100 | 100 | 99.9 ± 1.9 | 90.5 ± 13.2 |
| | 7 | 100 | 99.3 ± 1.2 | 96.3 ± 5.0 | 96.4 ± 2.6 |
| | 8 | 98.8 ± 1.4 | 100 | 97.3 ± 2.4 | 99.4 ± 1.0 |
| CD235a$^+$ | 5 | 100 | NA | NA | NA |
| | 6 | 100 | 69.7 ± 26.3 | 35.8 ± 22.6 | 38.1 ± 28.1 |
| | 7 | 100 | 60.1 ± 7.6 | 19.0 ± 9.2 | 11.6 ± 8.3 |
| | 8 | 99.0 ± 1.5 | 19.4 ± 7.7 | 5.2 ± 2.5 | 11.8 ± 5.4 |

TABLE 1-continued

CFC depletion by antibodies against hematopoietic markers

| Depleted cell subset | Day of differentiation | CFC depletion, % | | | |
|---|---|---|---|---|---|
| | | E-CFC | Mix-CFC | GM-CFC | M-CFC |
| CD41a+ | 5 | 55.8 ± 18.0 | NA | NA | NA |
| | 6 | 87.4 ± 9.6 | 20.8 ± 16.1 | 37.7 ± 23.7 | 35.5 ± 27.3 |
| | 7 | 93.2 ± 9.3 | 31.6 ± 10.7 | 9.0 ± 5.6 | 12.7 ± 9.6 |
| | 8 | 87.6 ± 13.3 | 4.1 ± 3.5 | 7.8 ± 6.6 | 11.3 ± 8.2 |
| CD45+ | 5 | <1 | NA | NA | NA |
| | 6 | <1 | <1 | <1 | <1 |
| | 7 | 4.7 ± 4.2 | 50.3 ± 6.5 | 46.2 ± 16.9 | 49.9 ± 17.5 |
| | 8 | <1 | 87.4 ± 11.7 | 56.4 ± 13.1 | 75.0 ± 9.3 |

Indicated cell subsets were depleted from hESC/OP9 cocultures by negative MACS technique using FITC/PE-conjugated specific mAbs and anti-FITC/PE secondary MicroBeads. Isotype-matched control mAbs were used for non-specific depletion control.
Depletion of cell subsets was in the range of 85-97% as determined by flow cytometry.
MACS-processed cell samples were tested for erythroid (E), mixed (Mix) and myeloid (GM, M) CFCs by MethoCult assay.
CFC depletion (%) was calculated by formula: 1 − (CFC counts in specific mAb-depleted sample ÷ CFC counts in isotype control mAb-treated sample) × 100.
Results are the mean ± SD of 4 independent experiments with H1 (n = 2) and H9 (n = 2) cells.
NA indicates not applicable (no CFC detection in the isotype control mAb-treated samples). By negative selection analysis, CFC depletion values (%) reflect the proportion of CFCs expressing a depletory marker.
CD43 was the only cell marker expressed by all CFC types throughout hESC/OP9 coculture.

CD43 Discriminates hESC-Derived Hematopoietic from Endothelial Cells

Figure 2:
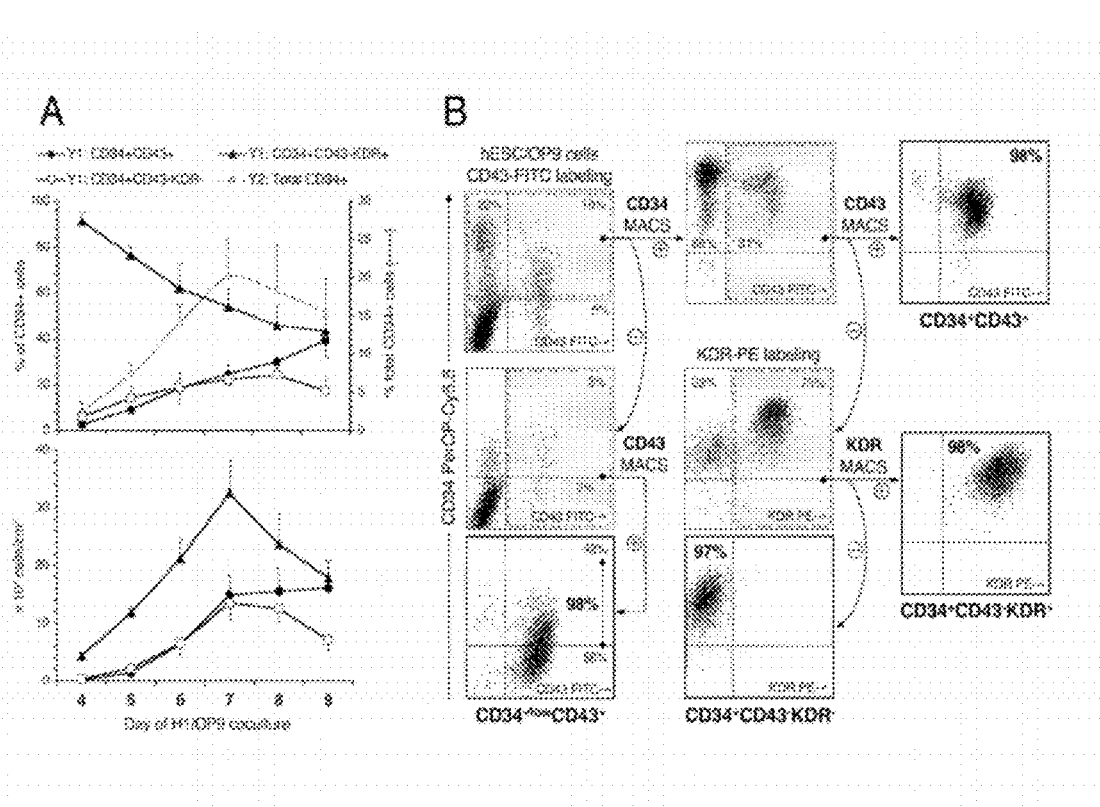
FIG. 2. Developmental kinetics and sorting strategy of CD34$^+$ subsets. (A) Kinetic analysis of CD34$^+$ subsets in H1/OP9 coculture. Indicated CD34$^+$ subsets were analyzed by FACS within gated CD34$^+$ population, and represented on the upper graph as % of CD34$^+$ cells (left Y1-axis). Total CD34$^+$ cells (%) are depicted by dashed trend line (right Y2-axis). The lower graph shows absolute numbers of respective CD34$^+$ subsets. Results are the mean±SD from 4 independent experiments. (B) Flow diagram of multi-parameter MACS separation of CD34$^+$ subsets showing a FACS analysis of target cell populations throughout the sorting procedure. Positive and negative MACS fractions are indicated by arrows marked with + and − circles, respectively. Values within dot-plots indicate % of cells in respective quadrants. The representative experiment is shown.
Figure 3:
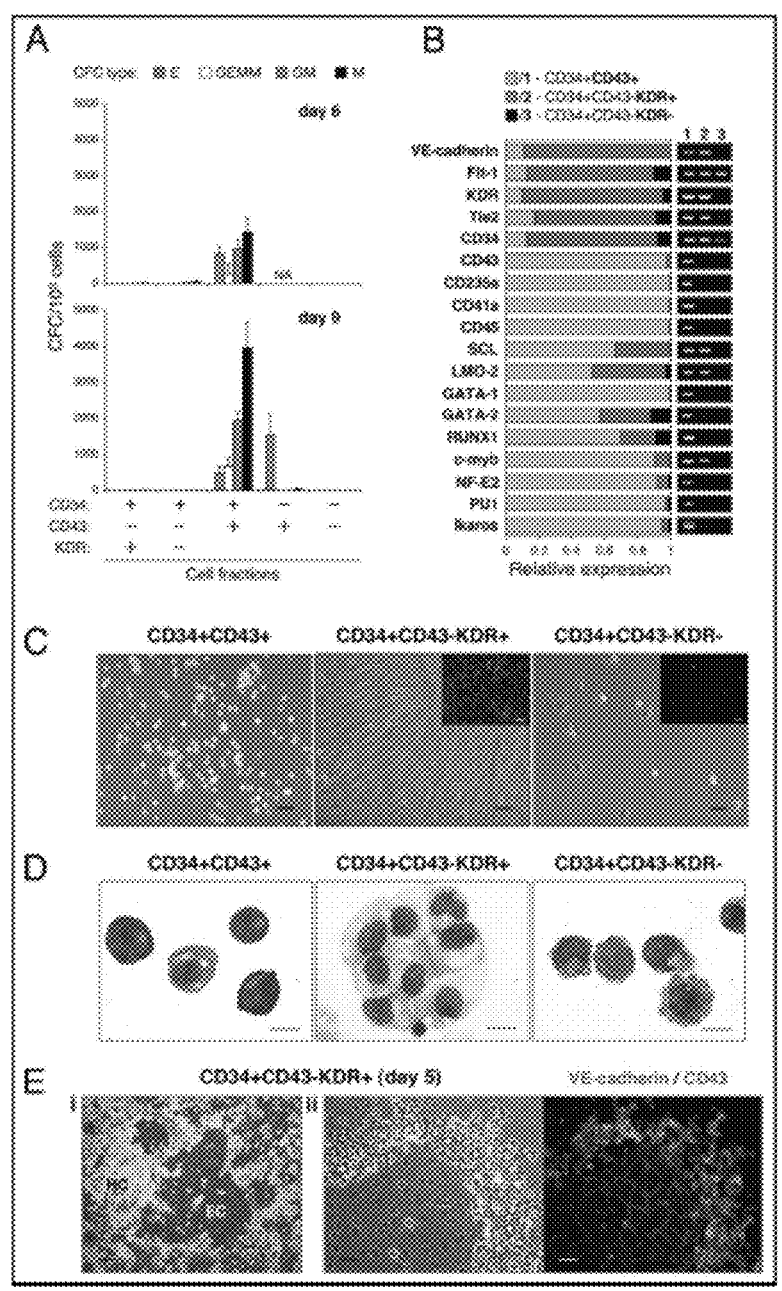
FIG. 3. Hematopoietic and endothelial potential of CD34$^+$ subsets. (A) CFC potential of MACS-sorted CD34$^+$ subsets with indicated phenotype (+/− chart) was tested using MethoCult GF+ assay. Results are the mean±SD from 9 independent experiments with H1 (n=6) and H9 (n=3) cells. NA indicates not applicable (subset was not detected/sorted). (B) Quantitative RT-PCR analysis of CD34$^+$ subsets on day 6 of H1/OP9 coculture. The stacked bar graph shows expression levels of indicated transcripts represented by relative units. qPCR results are the means from 3 independent experiments. Representative agarose gel electrophoresis of qPCR products is shown. (C) Endothelial culture of CD34$^+$ subsets isolated on day 6 of H1/OP9 coculture. Photographs show 5-day culture of indicated CD34$^+$ subsets in endothelial conditions (scale bar is 50 µm). Inserts show VE-cadherin expression (scale bar is 50 µm). VE-cadherin was stained by anti-VE-cadherin Ab (goat IgG; R&D Systems) followed by anti-goat IgG-AlexaFluor-488 conjugate (green fluorescence; Molecular Probes). Cell nuclei were visualized by DAPI staining (blue fluorescence). Fluorescent images were composed using Adobe Photoshop software (Adobe Systems Inc., San Jose, Calif.). The representative experiment is shown. Identical results were obtained with CD34$^+$ subsets isolated on day 9 (H1, H9) and day 6 (H9). (D) Wright-stained cytospins of CD34$^+$ subsets isolated on day 9 of H1/OP9 coculture (scale bar is 10 µm). (E) CD34$^+$CD43$^-$KDR$^+$ cells isolated on day 5 of H1/OP9 coculture were cultured 6 days with fresh OP9 cells (i) or without feeder cells (ii) in StemSpan serum-free medium (Stem Cell Technologies) supplemented with 2% FBS (HyClone), Ex-Cyte (1/500; Serological Corporation, Norcross, Ga.), 10 ng/ml bFGF, 50 ng/ml SCF, 10 ng/ml TPO, 20 ng/ml IL-6. Central endothelial clusters (EC) surrounded by proliferating hematopoietic clusters (HC) were observed in coculture with OP9 cells (i; scale bar is 100 µm). Similar hematoendothelial colonies were formed in feeder-free cultures (ii; scale bar is 50 µm); bright-field (left panel) and fluorescent (right panel) photographs show the same colony stained with anti-CD43 mAb (BD Pharmingen) and anti-VE-cadherin Ab (goat IgG; R&D Systems) followed by anti-mouse IgG-AlexaFluor-488 (green fluorescence) and anti-goat IgG-AlexaFluor-555 conjugates (red florescence; Molecular Probes). Note a clear separation of the hematopoietic and endothelial cells by CD43 staining: all rounded hematopoietic cells are CD43$^+$, but adherent VE-cadherin$^+$ endothelial cells are CD43$^-$.

Because CD43+ cells retained KDR expression up to day 7 of differentiation (FIG. 1D), it was unclear whether CD43 discriminates hematopoietic from endothelial cells. FACS analysis revealed that based on the expression of KDR and CD43, CD34+ cells could be subdivided into three major subsets: (1) CD34+CD43+, (2) CD34+CD43−KDR+, and (3) CD34+CD43−KDR− (FIG. 1D). As shown in FIG. 2A, the majority of early CD34+ cells (day 4) were KDR+ and CD43−. With advanced differentiation, CD34+CD43+ and CD34+CD43:KDR− subsets gradually increased, while a proportion of CD34+CD43−KDR+ cells decreased. CD34+ subsets were isolated on day 6 and 9 of differentiation as depicted in FIG. 2B and assayed for CFC potential or cultured with endothelial growth factors. As expected, positive selection of CD43+ cells resulted in recovery of all CFC types from CD34+ population (FIG. 3A). The number of CFCs within CD43− fractions remained negligible. In the same time, only CD34+CD43− KDR+ cells readily formed the monolayer of VE-cadherin+ cells when cultured in endothelial conditions (FIG. 3C). CD34+CD43+ cells remained in suspension and did not give rise to adherent cells up to 10 days of endothelial culture. CD34+CD43− KDR− cells produced neither VE-cadherin+ nor proliferating cells in endothelial conditions. Morphologically, the majority of CD34+CD43+ cells demonstrated a high nuclear-to-cytoplasm ratio, characteristic for hematopoietic blasts; however, more mature erythroid cells could be also found (FIG. 3D). CD34+CD43−KDR+ cells had typical endothelial morphology. Analysis of gene expression by qRT-PCR revealed that CD34+CD43+ cells expressed other hematopoietic markers (CD235a, CD41a, CD45) and transcription factors essential for hematopoietic commitment (SCL, LMO-2, RUNX1, c-myb, GATA-2) and specification of erythro-megakaryocytic (SCL, LMO-2, GATA-1, NF-E2) and lymphomyeloid (c-myb, PU1, Ikaros) lineages. In contrast, predominant expression of VE-cadherin, Flt-1, KDR and Tie2 in CD34+CD43−KDR+ cells reflected their endothelial potential (FIG. 3B).

To confirm that CD34+CD43−KDR+ cells represent endothelial cells, we evaluated their phenotype and functional potential. As shown in FIG. 4A, isolated CD34+ CD43−KDR+ cells were positive for endothelial markers VE-cadherin and CD31. They also possessed a distinctive expression of CD90 and CXCR4 (not shown) and α4-integrin (CD49d, VLA-4; FIG. 4D). In culture, these cells expressed markers of mature endothelial cells eNOS and vWF, and were capable of efficient Ac-LDL incorporation (FIG. 4B). When plated on MATRIGEL matrix, CD34+ CD43−KDR+ cells formed typical vascular tubes (FIG. 4C). Another feature of endothelial cells is the ability to up-regulate expression of VCAM-1 and ICAM-1 adhesion molecules in response to pro-inflammatory factors (Carlos T M, et al., Blood 1994; 84:2068-2101). As shown in FIG. 4D, CD34+CD43−KDR+ cells up-regulated ICAM-1 expression and became VCAM-1+ after treatment with TNF. This effect was specific and was not observed for VLA-4. Collectively, these data provide evidence that CD34+CD43−KDR+ cells isolated after 6 days of hESC/OP9 coculture represent endothelial cell population.

To further evaluate whether CD34+CD43+ and CD34+ CD43−KDR+ cells are committed to hematopoietic and endothelial development, respectively, we cultured these cells with fresh OP9 cells in presence of hematopoietic and endothelial growth factors (SCF, TPO, IL-6, bFGF). No hematopoietic cell production was detected from CD34+ CD43−KDR+ cells and no endothelial differentiation was observed from CD34+CD43+ cells isolated as early as day 6 of differentiation (not shown). However, CD34+CD43− KDR+ cells at earlier stages of differentiation (day 5) gave rise to hematoendothelial colonies upon coculture with OP9 cells or in feeder-free conditions (FIG. 3E). These colonies arose from primary endothelial clusters, which were formed during the first 4 days of the culture and subsequently gave rise to peripheral expansion of hematopoietic cells. In parallel cultures of CD34+CD43+ cells (day 5), such colonies were not observed, indicating that hematoendothelial precursors have primarily endothelial-like characteristics and reside in CD34+CD43−KDR+ population up to 5 days of differentiation.

The developmental potential of CD34+CD43−KDR− cells remains unclear. These cells lack detectable hematoendothelial potential either in direct assays or upon OP9 coculture. Cytospin preparations revealed that CD34+CD43−KDR− cells have a relatively high nuclear-to-cytoplasm ratio, a kidney-shaped or irregular nucleus and dark-blue cytoplasm (FIG. 3D). Phenotypically, CD34⁺CD43⁻KDR⁻ cells were similar to the majority of CD34⁻CD43⁻ cells in hESC/OP9 coculture (FIG. 4A). However, they could be distinguished by expression of CD73, low expression of CD44, higher expression of aminopeptidase N (CD13) and a unique bright expression of dipeptidyl-peptidase IV (CD26). These features are consistent with cells of mesenchymal origin and indicate that CD34⁺CD43⁻KDR⁻ cells may develop in hESC/OP9 coculture through a distinct non-hematoendothelial differentiation pathway.

In addition to CD34⁺CD43⁺ cells, we identified a small population of CD34$^{-/low}$CD43⁺ cells (FIG. 2B) that expressed CD235a (not shown) and formed only E-CFCs in MethoCult assay (FIG. 3A). These features are in agreement with CFC depletion experiments described above and indicate that CD34$^{-/low}$CD43⁺ cells represent erythroid progenitors at an advanced stage of maturation.

Altogether, these results demonstrate that CD43 expression discriminates hematopoietic from endothelial cells and signifies commitment to hematopoietic lineage.

Identification of Functionally Distinct CD43⁺-Hematopoietic Progenitors

As demonstrated above, CD43⁺ hematopoietic progenitors generated in hESC/OP9 coculture included CD41a⁺, CD235a⁺ and CD45⁺ cells (FIG. 1D). Phenotypic analysis of isolated CD43⁺ cells revealed that a major subset of CD43⁺ cells co-expressed CD235a and CD41a, while CD43⁺CD41a⁻CD235a⁻ subpopulation contained CD45⁺ and CD45⁻ cells (FIG. 5A). Therefore, PE-labeled CD235a and CD41a mAbs were combined and used with APC-labeled CD45 mAb to define three main CD43⁺ subsets: (1) CD43⁺CD41a/CD235⁺CD45⁻, (2) CD43⁺CD41a/CD235a⁻CD45⁻, and (3) CD43⁺CD41a/CD235a⁻CD45⁺ (FIG. 5A). Kinetic analysis of CD43⁺ subsets during hESC/OP9 coculture demonstrated that first E-CFCs appeared coincidentally with first CD43⁺CD41a/CD235a⁺CD45⁻ cells (days 4-5), first GEMM- and GM/M-CFCs emerged along with CD43⁺CD41a/CD235a⁻CD45⁻ cells (day 6), and a surge in GM/M-CFCs on day 7 was associated with the appearance of CD43⁺CD41a/CD235a⁻CD45⁺ cells (FIG. 5B). Since no lymphomyeloid or other tested markers (CD11b, CD14, CD2, CD3, CD7, CD19, CD38, HLA-DR) were detected either on CD34⁺ or CD43⁺ cells during hESC/OP9 coculture (not shown), we considered CD43⁺CD41a/CD235a⁻ cells as lineage-negative (Lin⁻) and designated the defined-above CD43⁺ subsets as (1) CD43⁺CD41a/CD235a⁺, (2) CD43⁺CD45⁻Lin⁻, (3) CD43⁺CD45⁺Lin⁻, respectively.

FACS-isolated CD43⁺ subsets (FIG. 5C) were examined for morphology, CFC potential and gene expression profile. All subsets displayed morphology similar to hematopoietic blasts: large nucleus with multiple, often elongated, prominent nucleoli and scant amount of basophilic cytoplasm (FIG. 5D). However, some distinctive features could be noticed. CD43⁺CD45⁻Lin⁻ cells were smaller and had the highest nucleus-to-cytoplasm ratio. CD43⁺CD45⁺Lin⁻ cells were larger and had more plentiful cytoplasm, often with a single large light-pink granule. CD43⁺CD41a/CD235a⁺ cells were variable in size and contained occasional erythroblastoid cells (FIG. 5D).

CFC potential of CD43⁺ cell subsets was tested using FBS-containing methylcellulose medium and serum-free collagen assay adapted for the simultaneous detection of E- and Mk-CFCs. As shown in FIG. 6A, CD43⁺CD41a/CD235a⁺ cells yielded E- and Mk-CFCs confirming their restricted erythro-megakaryocytic potential. Accordingly, in this population, qRT-PCR analysis revealed the highest expression levels of GATA-1 and NF-E2 transcription factors (FIG. 6B), which play a critical role in the erythromegakaryocytic lineage commitment and differentiation (Shivdasani R A., *Stem Cells* 2001; 19:397-407). In addition, a minor CD45⁺ subpopulation expressing CD41a/CD235⁺ (FIG. 5C) also produced only E- and Mk-CFCs (FIG. 6A).

Figure 6C:
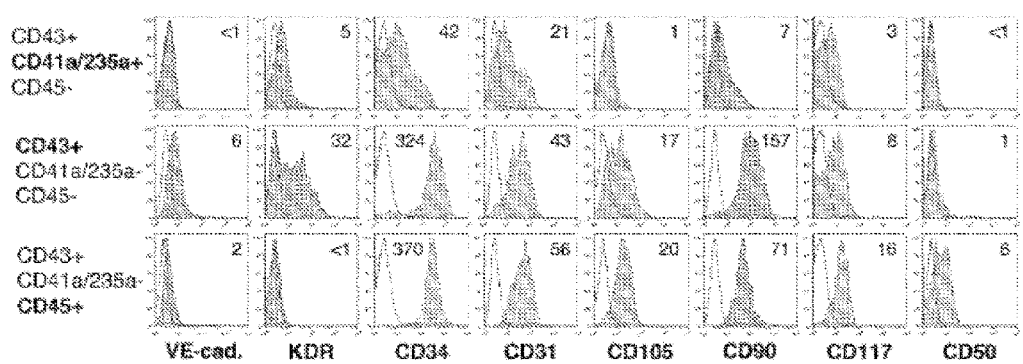

In contrast to CD43⁺CD41a/CD235⁺ cells, multilineage CFC potential was strictly associated with CD43⁺CD45$^{-/+}$Lin⁻ subsets. Notably, all GEMM- and GM/M-CFCs first-detectable on day 6 of hESC/OP9 coculture were recovered by selection of the rare CD43⁺CD45⁻Lin⁻ cells (FIG. 6A). Gene expression analysis revealed the highest levels of SCF-R (c-kit), transcription factors associated with definitive hematopoietic potential (RUNX1, c-myb, HoxB4), and markers of lymphomyeloid commitment (PU1, mb1, IL7Rα) in CD43⁺CD45$^{-/+}$Lin⁻ subsets (FIG. 6B). Moreover, Flt-3 and GATA-3 were restricted to these populations. By phenotype, CD43⁺CD45$^{-/+}$Lin⁻ subsets could be distinguished from CD43⁺CD41a/CD235⁺ cells by endoglin (CD105) expression, and higher expression of CD90 and CD34 (FIG. 6C). Remarkably, CD43⁺CD45$^{-/+}$Lin⁻ cells contained KDR subpopulation and expressed VE-cadherin and Flt-1 endothelial markers, which were all down-regulated in CD43⁺CD45⁺Lin⁻ cells (FIG. 6B,C). CD43⁺CD41a/CD235⁺ cells retained a low level of KDR expression, but VE-cadherin, Flt-1 and CD105 were almost undetectable in this population (FIG. 6B,C). CD50 (ICAM-3), suggested as early marker of hematopoietic progenitors in fetal bone-marrow CD34⁺CD38⁻ population, (Waller E K, et al., *Blood* 1995; 85:2422-2435) was weakly expressed only on CD45⁺ cells.

The sustained proliferation and establishment of long-term lymphomyeloid cultures are distinctive features of definitive hematopoietic progenitors (Godin I, et al., *Nat Rev Immunol.* 2002; 2:593-604). To address the lymphoid and long-term myeloid potential, we cultured isolated CD43⁺ subsets on MS-5 stromal cells in conditions that support differentiation of hESC-derived CD34⁺ cells into B- and NK cells, granulocytes and macrophages (Vodyanik M A, et al., *Blood* 2005; 105:617-626). As shown in FIG. 6D, in MS-5 cocultures supplemented with myeloid cytokine combination (SCF, G-CSF, IL-3), CD43⁺CD45$^{-/+}$Lin⁻, but not CD43⁺CD41a/CD235a⁺ cells displayed vigorous proliferation associated with retention of myeloid CFCs up to 6 weeks of culture. In MS-5 cocultures with SCF, Flt3-L and IL-7, commitment to lymphoid cell lineages determined by expression of NK– (CD3ε, CD3ζ) and B-cell (mb1, VpreB, pax-5) specific transcripts were also restricted to CD43⁺CD45$^{-/+}$Lin⁻ subsets.

Although both CD43⁺CD45⁻Lin⁻ and CD43⁺CD45⁺Lin⁻ cells contained multilineage progenitors, CD45⁺ cells displayed several features indicating their advanced lineage-restricted specification, predominantly toward myeloid pathway: (1) CD45⁺ cells were highly enriched in myeloid CFCs (FIG. 6A) and expressed early marker of myeloid commitment—myeloperoxidase (MPO) (FIG. 6B); (2) CD90, GATA-3 and RUNX1 were down-regulated in CD45⁺ cells, while Flt-3 was strongly up-regulated (FIG. 6B,C); (3) critical markers of B-lymphoid commitment pax-5 and VpreB, which were reproducibly detected in MS-5 cocultures with CD43⁺CD45⁺Lin⁻ cells, were undetectable in parallel cultures with CD45⁺ cells, while NK-specific transcripts (CD3ε, CD3ζ) were highly expressed in both cultures (FIG. 6D).

Thus, we identified two major populations of hematopoietic progenitors generated during one-step hESC/OP9 coculture: (1) CD43⁺CD235a⁺CD41a⁺CD45⁻ pre-committed erythro-megakaryocytic, and (2) CD43$^+$CD45$^{-/+}$Lin$^-$ multilineage progenitors. Based on CD45 expression, multilineage progenitors could be subdivided on the (1) early CD43$^+$CD45$^-$Lin$^-$ progenitors with lymphomyeloid potential, and (2) late CD43$^+$CD45$^+$Lin$^-$ progenitors undergoing progressive myeloid commitment.

C. Discussion

We report a novel observation that CD43 defines early hematopoietic progenitors and discriminates hematopoietic from endothelial cells upon hESC differentiation in vitro. CD43 (also known as leukosialin, sialophorin) is one of the most prevalent leukocyte transmembrane sialoglycoproteins (Carlsson S R, et al., *J Biol. Chem.* 1986; 261:12779-12786) expressed exclusively on cells of hematopoietic lineage, including hematopoietic stem cells, (Moore T, et al., *J Immunol.* 1994; 153:4978-4987) but excluding mature erythrocytes and B-cell subsets (Remold-O'Donnell E, et al., *Blood* 1987; 70:104-109; Wiken M, et al., *Scand J Immunol.* 1988; 28:457-464). CD43 has a highly conserved across species cytoplasmic domain and mucin-like extracellular domain, which is extensively O-glycosylated (Shelley C S, et al., *Proc Natl Acad Sci USA* 1989; 86:2819-2823; Remold-O'Donnell E, et al., *J Exp Med.* 1984; 159:1705-1723). Cytoplasmic domain of CD43 interacts with cytoskeletal proteins and transmits signals that regulate a variety of intracellular signal transduction pathways involved in cell activation, proliferation, and survival (Ostberg J R, et al., *Immunol Today* 1998; 19:546-550). Notably, cross-linking of CD43 induces apoptosis of bone marrow clonogenic progenitors, but not hematopoietic stem cells (Bazil V, et al., *Blood* 1996; 87:1272-1281). The high level of glycosylation and net negative charge explains anti-adhesive properties of the CD43 molecule which have been demonstrated in a number of studies (Manjunath N, et al., *Nature* 1995; 377:535-538; Ardman B, et al., *Proc Natl Acad Sci USA* 1992; 89:5001-5005). CD43 also transmits signals enabling other ligand-receptor interactions to promote cell adhesion, (Anzai N, et al., *Blood* 1999; 93:3317-3326; Kuijpers T W, et al., *J Immunol.* 1992; 149:998-1003; Sanchez-Mateos P, et al., *Blood* 1995; 86:2228-2239) and may function as a ligand for ICAM-1 and E-selectin molecules expressed on endothelial cells (Fuhlbrigge R C, et al., *Blood* 2005; 107:1421-1426; Matsumoto M, et al., *J Immunol.* 2005; 175:8042-8050; Rosenstein Y, et al., *Nature* 1991; 354:233-235). It has been proposed that CD43 can act as a gateway to facilitate certain cell contacts (Ostberg J R, et al., *Immunol Today* 1998; 19:546-550). Early expression of CD43 on hESC-derived hematopoietic progenitors reported in the present study may also indicate a possible role of CD43 in hematopoietic development, including acquisition of anti-adhesive properties by emerging hematopoietic cells.

In mice, the earliest-appearing multipotent hematopoietic progenitors in yolk sac and AGM or derived from ESCs in vitro are CD45$^-$ (Li W, et al., *Stem Cells Dev.* 2005; 14:44-54; Mikkola H K, et al., *Blood* 2003; 101:508-516; Bertrand J Y, et al., *Proc Natl Acad Sci USA* 2005; 102:134-139) and can be identified by expression of CD41 (Mikkola H K, et al., *Blood* 2003; 101:508-516; Bertrand J Y, et al., *Proc Natl Acad Sci USA* 2005; 102:134-139; Ferkowicz M J, et al., *Development* 2003; 130:4393-4403; Mitjavila-Garcia M T, et al., *Development* 2002; 129:2003-2013; Emambokus N R, et al., *Immunity* 2003; 19:33-45). Additionally, MAC-1 (CD11b) and α4-integrin (CD49d) were proposed as markers of early hematopoietic precursors (Taoudi S, et al., *Development* 2005; 132:4179-4191; Ogawa M, et al., *Int Rev Immunol.* 2001; 20:21-44; Sanchez M J, et al., *Immunity* 1996; 5:513-525). We demonstrated that the earliest hESC-derived multipotent hematopoietic progenitors expressed CD43, but not CD41a and CD11b. Although human hematopoietic progenitors were CD49d$^+$ (not shown), this molecule was also expressed on hESC-derived endothelial cells (FIG. 4D); thus, it was not useful for discrimination between these two lineages. We have not found reports related to expression of CD43 on hematopoietic cells during early embryonic or ESC-derived hematopoiesis in mice. However, striking similarities in CD43 expression on human and mouse bone marrow hematopoietic stem cells have been reported, (Moore T, et al., *J Immunol.* 1994; 153:4978-4987) and therefore it is reasonable to expect that expression of CD43 during hematopoietic development in mice will follow the pattern that we described here for hESCs.

Emergence of clonogenic hematopoietic progenitors before CD45 expression has also been observed following hESC differentiation on S17 stromal cells (Kaufman D S, et al., *Proceedings of the National Academy of Sciences of the United States of America.* 2001; 98:10716-10721) and embryoid body differentiation (Zambidis E T, et al., *Blood* 2005; 106:860-870; Ng E S, et al., *Blood* 2005; 106:1601-1603). It is likely that similar to OP9 system, early CD45$^-$ hematopoietic progenitors described in other differentiation systems might be identified by expression of CD43. CD43$^+$CD45$^-$ Lin$^-$ hematopoietic blast cells morphologically similar to hESC-derived CD43$^+$CD45$^-$Lin$^-$ hematopoietic progenitors have been described in human embryonic and fetal liver, (Timens W, et al., *Microsc Res Tech.* 1997; 39:387-397) suggesting that these cells are an integral part of hematopoietic development in vivo.

Studies in mouse ESC/OP9 cocultures have demonstrated a step-wise divergence of lineage-restricted primitive hematopoietic progenitors from VEGF-R2$^+$VE-cadherin$^-$ mesodermal precursors and multilineage definitive progenitors from later VEGF-R2$^+$VE-cadherin$^+$ endothelial-like precursors (Nishikawa S I, et al., *Development* 1998; 125: 1747-1757; Fujimoto T, et al., *Genes Cells* 2001; 6:1113-1127; Endoh M, et al., *EMBO J.* 2002; 21:6700-6708; Nakano T, et al., *Science* 1996; 272:722-724). Using CD43 as the earliest pan-hematopoietic marker, we found a similar two-step divergence of hematopoietic elements in hESC/OP9 coculture. In fact, CD43$^+$CD41a/CD235a$^+$ erythro-megakaryocytic progenitors develop first on day 4-5 of differentiation followed by CD43$^+$CD45$^-$Lin$^-$ multilineage progenitors on day 6 (FIG. 1D, 5B). CD43$^+$CD45$^-$ Lin$^-$ multilineage progenitors retain expression of VE-cadherin, KDR and CD105 endothelium-associated molecules, highly suggesting that they are derived from endothelial-like precursors. In contrast, CD43$^+$CD41a/CD235a$^+$ cells retain expression of only KDR, pointing to earlier precursors for this lineage. It can be suggested that erythro-megakaryocytic progenitors diverge from the earliest CD34$^+$KDR$^+$ precursors at their pre-endothelial commitment stage, most likely through CD34$^+$CD235a$^+$ intermediates. During subsequent endothelial commitment, CD34$^+$KDR$^+$ precursors up-regulate VE-cadherin and CD105 expression and acquire the capacity to generate multilineage hematopoietic progenitors and endothelial cells (FIG. 7). Although our study identifies CD43 as a marker of committed hematopoietic progenitors, phenotypic features that discriminate hemogenic from committed endothelial cells are currently unclear, and whether VE-cadherin, CD105 or other endothelial markers can separate hemogenic endothelium from earlier CD34$^+$KDR$^+$ hemogenic precursors remains to be determined. Prospective identification of these precursors will facilitate studies of primitive versus definitive hematopoiesis in hESC/OP9 coculture. Preliminary analysis of single erythroid colonies generated from H1-derived CD43$^+$CD41a/CD235a$^+$ cells shows that all colonies express embryonic hemoglobin ($\zeta$/$\epsilon$-chains), however, about 40% colonies on day 6 express adult hemoglobin ($\beta$-chain), and this proportion increases up to 90% on day 9. Thus, primitive erythroid progenitors ($\zeta$/$\epsilon^+$ $\beta^-$) may predominate on early days (4-6) of differentiation, while definitive ones ($\beta^+$) (Peschle C, et al., Nature 1985; 313:235-238) progressively contribute to CD43$^+$CD41a/CD235a$^+$ population on later days. Because the first-appearing CD43$^+$ cells already express CD235a and seem to originate from CD34$^+$CD235a$^+$CD43$^-$ cells (FIG. 1D), this transient population that peaked on day 5 (FIG. 1C) may represent immediate precursors of primitive hematopoiesis in hESC/OP9 coculture.

In the present study, we defined CD43$^+$CD45$^-$Lin$^-$ cells as the earliest multilineage definitive progenitors developed from hESCs in vitro. These cells have lymphomyeloid potential and molecular phenotype (SCL$^+$GATA-2$^+$GATA-3$^{high}$RUNX1$^{high}$c-myb$^+$ HoxB4$^+$) consistent with emerging hematopoietic precursors identified in human and mouse AGM region (Bertrand J Y, et al., Proc Natl Acad Sci USA 2005; 102:134-139; Labastie M C, et al., Blood 1998; 92:3624-3635). Acquisition of CD45 expression by these cells was accompanied with dramatic increase of myeloid clonogenic progenitors, loss of B lymphoid potential, down-regulation of GATA-3 and RUNX1, and up-regulation of MPO, PU1 and Flt-3, that altogether signify a progressive myeloid commitment in CD45$^+$ cells (findings summarized in FIG. 7). It is possible that myeloid propensity of CD45$^+$ cells was only influenced by differentiation conditions in OP9 culture. However, recent observations in mouse embryo at day 10.5 postcoitum demonstrated that multipotent precursors from AGM region that generate lymphoid cells and possess long-term repopulating potential differ from their fetal liver and adult counterpart by lack or low level of CD45 expression, while CD45$^+$ cells represent already committed myeloid cells (Bertrand J Y, et al., Proc Natl Acad Sci USA 2005; 102:134-139). To our knowledge, presence of CD45$^-$ hematopoietic precursors in human yolk sac or AGM has not been described yet. Since ESC differentiation in vitro recapitulates many aspects of embryonic development, (Mikkola H K, et al., Blood 2003; 101:508-516; Keller G, et al., Mol Cell Biol. 1993; 13:473-486; Gadue P, et al., Exp Hematol. 2005; 33:955-964) we presume that the sequence of hESC hematopoietic development described here reflects, at least in some degree, events occurring in vivo in human yolk sac and AGM region.

In summary, we identified CD43 as the earliest pan-hematopoietic marker during hESC differentiation in vitro, and described functionally distinct populations of hematopoietic progenitors generated from hESCs. These findings provide a means for direct detection and prospective analysis of hESC-derived hematopoietic progenitors, and are important for further studies of hematoendothelial divergence in hESCs.

2. Human Embryonic Stem Cell-Derived CD34+ Cells: Efficient Production in the Co-Culture with OP9 Stromal Cells and Analysis of Lymphohematopoietic Potential A. Introduction Human ES (hES) cells represent a unique population of cells capable of self-renewal and differentiation. hES cells give rise to tissues from all three germ layers upon injection into immunodeficient mice or when induced to form embryoid bodies in vitro (Schuldiner M, et al., Proceedings of the National Academy of Sciences of the United States of America. 2000; 97:11307-11312; Thomson J A, et al., Science 1998; 282:1145-1147). Recently, the potential of hES cells to differentiate into hematopoietic lineage has been demonstrated. During embryoid body differentiation or upon co-culture with S17 bone marrow stromal cell line, hES cells give rise to endothelial cells with hemangioblastic properties (Wang L, et al., Immunity 2004; 21:31-41) and colony-forming cells (CFCs) (Kaufman D S, et al., Proceedings of the National Academy of Sciences of the United States of America. 2001; 98:10716-10721; Chadwick K, et al., Blood 2003; 102:906-915; Zhan X, et al., Lancet 2004; 364:163-171). The addition of a combination of cytokines and bone-morphogenic protein-4 (BMP-4) strongly promotes hES cell hematopoietic differentiation during embryoid body development (Chadwick K, et al., Blood 2003; 102: 906-915). These results clearly demonstrate the utility of hES cells as an alternative source of hematopoietic precursors that potentially can be used for studies of hematopoietic ontogeny and hematopoietic cell transplantation in humans. However, this requires reproducible methods for large-scale production of hematopoietic stem cells from hES cells.

The macrophage colony stimulating factor (M-CSF)-deficient stromal cell line OP9 has been used successfully to induce mouse ES cell differentiation into myeloid, lymphoid, erythroid, and megakaryocytic lineage cells (Nakano T, et al., Science 1994; 265:1098-1101; Nakano T, et al., Science 1996; 272:722-724; Eto K, et al., Proceedings of the National Academy of Sciences of the United States of America. 2002; 99:12819-12824). Here we describe OP9 co-culture for hematopoietic differentiation of hES cells. OP9 co-culture allowed to observe the process of hematopoietic differentiation of hES cells and was superior to S17 and MS-5 co-culture in the production of CD34+ cells and CFCs. We demonstrated that CD34+ cells generated in the OP9 system gave rise to B, NK, and myeloid cell lineages, indicating that cells with definitive hematopoietic potential could be obtained from hES cells. Another important advantage of OP9 co-culture was the ability, within a short period of time and without added cytokines, to generate a large number of CD34+ cells that can be isolated using magnetic sorting. In addition, hES cells/OP9 co-culture could represent a powerful in vitro model for analyzing the earliest stages of hematopoietic development that are not accessible in human embryos.

B. Materials And Methods

Cell Culture

The hES cell lines (H1 passages 23-45 and H9 passages 27-38) were maintained in an undifferentiated state by weekly passage on mouse embryonic fibroblast (MEF) layers as previously described (Amit M, et al., Developmental Biology 2000; 227:271-278). At least 5 different batches of H1 and 3 different batches of H9 karyotypically normal cell lines were used. The OP9 mouse bone marrow stromal cell line was obtained from Dr. Toru Nakano (Research Institute for Microbial Diseases, Osaka University, Japan). This cell line was maintained on gelatinized 10 cm dishes (BD Bioscience, Bedford, Mass.) in OP9 growth medium consisting of $\alpha$-MEM (Invitrogen, Carlsbad, Calif.) supplemented with 20% non-heat-inactivated Defined Fetal Bovine Serum (FBS; HyClone Laboratories, Logan, Utah). Mouse bone marrow stromal cell lines S17 and MS-5 were obtained from Dr. Kenneth Dorshkind (University of California, Los Angeles) and the German Tissue Culture Collection, respectively. These cells were maintained in $\alpha$-MEM supplemented with 10% FBS (Invitrogen).

Hematopoietic Differentiation of hES Cells in Co-Culture with OP9, S17, and MS-5 Cells For hES cell differentiation, OP9 cells were plated onto gelatinized 6-well plates or 10 cm dishes in OP9 growth medium (see above). After formation of confluent cultures on days 4-5, a half of medium was changed and cells were cultured for an additional 3-4 days. Undifferentiated hES cells were harvested by treatment with 1 mg/ml collagenase IV (Invitrogen) and dispersed by scraping to maintain the cells in small clumps. Concurrently, hES cultures growing under the same conditions were used to obtain single cell suspension (as described below) for counting. The hES cells were added to OP9 cultures at a density of $1.5 \times 10^6/20$ ml per 10 cm dish, or $0.3 \times 10^6/4$ ml per well of a 6-well plate, in α-MEM supplemented with 10% FBS (HyClone) and 100 µM MTG (Sigma, St. Louis, Mo.). The hES cell/OP9 co-cultures were incubated for up to 10 days at 37° C. in normoxic conditions and 5% $CO_2$ with a half-medium change on days 4, 6, and 8. Cells were harvested every day, and single-cell suspension was prepared by treatment of the hES cell/OP9 co-cultures with collagenase IV (Invitrogen; 1 mg/ml in α-MEM) for 20 min at 37° C., followed by treatment with 0.05% Trypsin-0.5 mM EDTA (Invitrogen) for 15 min at 37° C. Cells were washed twice with PBS-5% FBS, filtered through a 100 µM cell strainer (BD Biosciences), counted, and used for clonogenic and flow-cytometric assays, and gene expression analysis. Culture and analysis of hES cells growing on S17 and MS-5 cell lines were performed in a similar manner.

Because comparable results were obtained for H1 and H9 hES cell/OP9 co-cultures, we reported pooled data for both cell lines in these studies.

Positive Selection of CD34+ Cells by Magnetic Sorting

A single-cell suspension from days 8-9 of hES cell/OP9 co-cultures, prepared as described above, was labeled with CD34 paramagnetic monoclonal antibodies (mAb) using Direct CD34 Progenitor Cell Isolation Kit (Miltenyi Biotech, Auburn, Calif.) as recommended by the manufacturer, and processed through an LS+ separation column attached to a Midi-MACS separation unit (Miltenyi Biotech) to obtain the magnet-retained fraction of purified CD34+ cells. Purity of isolated CD34+ cells, as determined by flow cytometry, was generally greater than 95% at a single column run, and cell viability, as evaluated by Trypan Blue exclusion, was always higher than 95%.

Clonogenic Progenitor Cell Assay

Hematopoietic clonogenic assays were performed in 35 mm low adherent plastic dishes (Stem Cell Technologies) using a 1 ml/dish of MethoCult GF+H4435 semisolid medium (Stem Cell Technologies) consisting of 1% methylcellulose, 30% FBS, 1% BSA, 50 ng/ml stem cell factor (SCF), 20 ng/ml granulocyte-macrophage colony stimulating factor (GM-CSF), 20 ng/ml IL-3, 20 ng/ml IL-6, 20 ng/ml granulocyte colony stimulating factor (G-CSF), and 3 units/ml erythropoietin. Cells from hES cell/OP9 co-culture were plated at various densities depending on the day of differentiation: 1-5 days—$2 \times 10^5$/ml; 6 day—$1 \times 10^5$/ml; 7-8 days—$5 \times 10^4$/ml; and 9-10 days—$2 \times 10^4$/ml. Sorted CD34+ cells were plated at $2 \times 10^3$/ml. Undifferentiated hES cells were tested at densities up to $5 \times 10^5$/ml, and no CFCs were found. All clonogenic progenitor assays were performed in duplicate. CFCs were scored after 14-21 days of incubation according to their colony morphology as erythroid (E-CFC), granulocyte, erythroid, macrophage, megakaryocyte (GEMM-CFC), granulocyte-macrophage (GM-CFC), and macrophage (M-CFC). Cytospin preparations from single colonies were made using a Cytospin centrifuge (Shandon, Pittsburgh, Pa.). The cytospins were fixed with methanol and stained with Wright stain (Sigma) to confirm the cell content of appropriate colonies. The frequency of CFC was calculated per $10^6$ total cells.

Simultaneous Lympho-Myeloid Differentiation of CD34+ Cells In Vitro

CD34+ cells were seeded on 6-well plates ($5 \times 10^4$ cells/well) with pre-established irradiated (50 Gy) monolayer of MS-5 stromal cells in the complete medium (4 ml/well) consisting of α-MEM supplemented with 10% FBS (HyClone), 100 µM MTG and following human cytokines: SCF—50 ng/ml; the class III receptor tyrosine kinase ligand (Flt3-L)—50 ng/ml; IL-3—10 ng/ml; IL-7—20 ng/ml (Peprotech, Rocky Hill, N.J.). Separate cultures were additionally supplemented with 20 ng/ml of IL-15 to induce NK cell maturation. A half of medium was changed every $5^{th}$ day with complete medium without IL-3. After 21 days of incubation, single cell suspension was harvested by treatment of CD34+/MS-5 co-cultures with collagenase IV/hyalouronidase IV solution (1 mg/ml and 0.05 mg/ml in α-MEM, respectively) for 20 min at 37° C., followed by treatment with non-enzymatic cell dissociation solution (Invitrogen) for 30 min at 37° C. Cells were used for flow cytometric and RT-PCR analysis.

Phenotype Analysis by Flow Cytometry

Cells were prepared in PBS containing 0.05% sodium azide, 1 mM EDTA, 2% FBS and '2% normal mouse serum (Sigma), and were labeled with a combination of monoclonal antibodies (mAbs). For analysis of perforin expression, cells were permeabilized using Fix&Perm reagents (Caltag, Burlingame, Calif.). Samples were analyzed using a FACSCalibur flow cytometer (BDIS, San Jose, Calif.) with CellQuest acquisition software (BDIS). List mode files were analyzed by FlowJo software (Tree Star, Inc., Ashland, Oreg.). The mAbs were preliminary tested for cross-reactivity with OP9 and mouse bone marrow mononuclear cells. Only those following mAbs without detectable cross-reactivity with murine cells were selected: KDR–PE (R&D Systems); CD19-APC, CD34-PerCP-Cy5.5, CD38-PE, CD117-PerCP-Cy5.5, HLA-DR-PE (BDIS); CD14-FITC, CD31-FITC, CD41a-OE, CD43-FITC, CD45-PE/APC, CD90-APC, CD164-FITC, CD184-APC, perforin-FITC (BD Pharmingen); CD56-PE, CD133-PE (Miltenyi Biotech); and CD10-APC, CD66b-FITC (Caltag). Control staining with appropriate isotype-matched control mAbs (BD Pharmingen) was included to establish thresholds for positive staining and background for linear-scaled mean fluorescence intensity (MFI). The percentage (%) of positive cells was calculated as % of positive cells stained with specific mAb-% of background staining with corresponding isotype control. The ΔMFI was calculated as MFI of cells stained with specific mAb-MFI of cells stained with corresponding isotype control. Linear-scaled MFI was used as an indicator of relative antigen density on given cells. Results were presented as a percent of positive cells and/or ΔMFI±standard deviation (SD).

Rhodamine 123 (Rho) Exclusion Assay $10^6$ isolated CD34+ cells were incubated with 0.1 µg/ml Rho (Molecular Probes, Eugene, Oreg.) in 1 ml of RPMI-1640 medium containing 15 mM HEPES and 2% FBS (assay medium), for 30 min at 37° C. Cells were washed with and resuspended in assay medium and incubated for 40 min at 37° C. without or with 50 µM verapamil (Sigma) to reveal Rho exclusion activity. After washing with PBS-FBS, cells were labeled with CD45-APC mAb, resuspended in PBS containing 2 µg/ml propidium iodide (PI; Sigma) and analyzed by flow cytometry. A minimum of $2 \times 10^5$ events from live-gated, PI-negative cells were acquired. $Rho^{low}$ cells were defined as those showing less fluorescence in the FL-1 channel than exhibited by verapamil-treated samples.

Aldehyde Dehydrogenase (ALDH) Staining

ALDH staining of CD34+ cells was performed using ALDEFLUOR kit (Stem Cell Technologies) according to instruction provided by manufacturer. Control samples were established using diethylaminobenzaldehyde (DEAB), an ALDH inhibitor. Cells were also stained for CD45, and dead cells were excluded using PI staining. Samples were analyzed by flow cytometry.

Immunocytochemistry

Cytospins of hES cells or isolated CD34+ cells were stained using anti-Oct-4 mAb (Santa Cruz Biotechnology, Santa Cruz, Calif.) and ABC peroxidase kit (Vector Laboratories, Burlingame, Calif.).

Gene Expression Analysis by Conventional and Real Time Quantitative PCR (QPCR)

Total RNA was isolated from cells using RNAwiz (Ambion, Austin, Tex.). Human bone marrow, thymus and fetal liver RNA were purchased from Clontech (Palo Alto, Calif.). All RNA samples were treated with DNAfree reagent (Ambion) to remove potentially contaminating DNA. The cDNA was prepared from 1 µg of total RNA using oligo(dT) primer (Ambion) and Omniscript RT kit (Qiagen, Valencia, Calif.). QPCR was performed using Brilliant SybrGreen QPCR kit (Stratagene, La Jolla, Calif.). The specified genes were amplified for 40 cycles, and PCR reactions were analyzed with ABI Prism 7700 (Applied Biosystems, Foster City, Calif.). Regular PCR was performed using Taq PCR kit (Qiagen) for each transcript to check the size of the amplified product and its sequencing to ensure authenticity. QPCR reactions were done using 2 µl of RT products per reaction according to the instruction from manufacturer with the annealing temperature optimized for each primer. Transcripts of target genes were amplified along with the housekeeping gene glyceraldehyde-3-phosphate dehydrogenase (GAPDH) using human specific primers. GAPDH was selected as the housekeeping gene since its expression remains constant during ES cell differentiation in culture (Murphy C L, et al., Tissue Eng. 2002; 8:551-559). Each reaction was performed in duplicate. All QPCR products were analyzed on 2.0% agarose gels to exclude false-positive readings due to primer dimers. Comparative quantification of the target gene expression in the samples was performed based on cycle threshold (Ct) normalized to GAPDH using the ΔΔCt method (Livak K J, et al., Methods 2001; 25:402-40). The relative expression of target genes in hES cell/OP9 co-cultures as well as hES cell-derived CD34+ and CD34− cell populations were compared with the level of the same gene expression in bone marrow samples using the following equation:

Fold differences=$2^{\Delta\Delta Ct}$, where $\Delta\Delta Ct=$
$\Delta Ct_{bone\ marrow} - \Delta Ct_{hES\ cells}$ and
$\Delta Ct_{bone\ marrow} = Ct_{target\ gene} - Ct_{GAPDH}$,
$\Delta Ct_{hES\ cells} = Ct_{target\ gene} - Ct_{GAPDH}$.

The primers used (Table 2), except β-actin primers, were human gene-specific and did not amplify cDNA from mouse cells (OP9, MS-5 and MEFs ).

C. Results

Distinctive Efficiency of OP9 Stromal Cells in the Induction of hES Cell Hematopoietic Differentiation Several bone marrow stromal cell lines have been shown to support hematopoietic differentiation of ES cells in mice and humans (Kaufman D S, et al., Proceedings of the National Academy of Sciences of the United States of America. 2001; 98:10716-10721; Nakano T, et al., Science 1994; 265:1098-1101; Mitjavila M T, et al., Experimental Hematology 1998; 26:124-134). To find the optimal bone marrow stromal cell line for induction of hematopoietic differentiation, we co-cultured hES cells on OP9, S17, and MS-5 cell lines. We found that the OP9 cell line was superior to both the MS-5 and S17 cell lines. After 7 days of culture, a substantial numbers of CD34+ cells and CFCs were generated in the OP9 co-culture, while significantly fewer CD34+ cells and CFCs were observed in the MS-5 and S17 co-cultures (FIGS. 8A and 8B). On day 4 of the OP9 co-culture, colonies morphologically similar to mesodermal colonies described in the mouse ES cell/OP9 co-culture appeared (Kitajima K, et al., Methods in Enzymology 2003; 365:72-83). These colonies displayed dense, elevated central portions composed of stacked, large, round cells (FIG. 8C). The hES cell colonies in MS-5 and S17 cultures were different and appeared as flat, doughnut-shaped groups of cells with empty centers that tended to spread peripherally (FIG. 8C).

Emergence of CD34+ Cells in hES Cell/OP9 Co-Culture is Associated with the Acquisition of Clonogenic Hematopoietic Potential and the Upregulation of Hematopoiesis-Associated Genes To examine the timeframe of hematopoiesis onset and to define the phenotype of early hematopoietic progenitors in the hES cell/OP9 co-culture, we evaluated CFCs and the expression of hematopoiesis-associated molecules on undifferentiated hES cells and on hES cells after 1 to 10 days of differentiation. hES cells maintained strictly in an undifferentiated state did not express CD34, CD31, CD43, CD41a, or CD45 (FIGS. 9A, and 10). In the OP9 co-culture, CD34+ cells first appeared on day 3 of culture and gradually peaked at day 7 (FIG. 9A). CD43+ and CD41a+ cells appeared 2 days later within CD34+ populations and gradually increased by day 10 of culture (FIG. 9A). The temporal kinetics of the CD31+ cells closely followed that of CD34+ cells; however, CD31+ cells were first seen one day after the appearance of CD34+ cells. CD45+ cells appeared much later, on day 8 of culture (FIG. 9A). FIG. 10 shows representative, flow-cytometric analysis of the expression of hematopoiesis-associated molecules by undifferentiated and differentiated hES cells on days 6 and 9 of OP9 co-culture.

Figure 4:
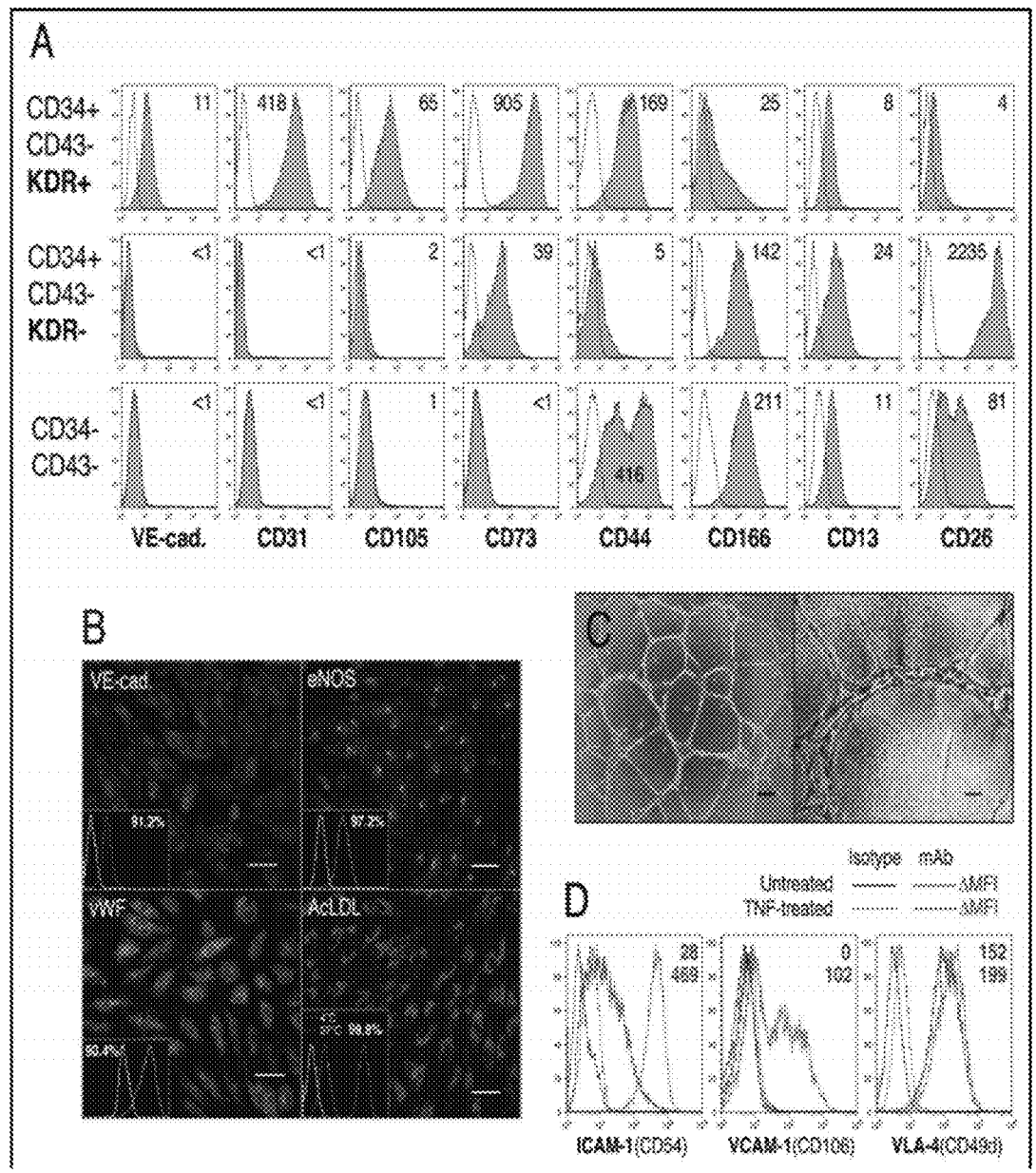
FIG. 4. Endothelial phenotype and function of CD34$^+$CD43$^-$KDR$^+$ cells isolated after 6 days of H1/OP9 coculture. (A) FACS analysis of KDR$^+$ and KDR$^-$ fractions of CD34$^+$CD43$^-$ cells isolated on day 9 of H1/OP9 coculture. Phenotype of CD34$^+$CD43$^-$KDR$^-$ cells was compared with phenotype of CD34$^-$CD43$^-$ cells obtained after depletion of CD34$^+$ and CD43$^+$ cells. Plots show isotype control (open) and specific mAb (tinted) histograms. Values within plots indicate specific mean fluorescence intensity (ΔMFI) calculated by formula: linear-scaled MFI of specific mAb-stained cells-linear-scaled MFI of isotype control mAb-treated cells. The representative experiment is shown. Similar results were obtained in 5 independent experiments with H1- and H9-derived CD34$^+$CD43$^-$KDR$^{+/-}$ cells isolated on day 6 (n=2) and day 9 (n=3) of differentiation. (B) CD34$^+$CD43$^-$KDR$^+$ cells were cultured 7 days in endothelial expansion conditions and examined for markers of mature endothelial cells. Immunofluorescent staining was performed with primary Abs against VE-cadherin (goat IgG; R&D Systems), von-Willebrand factor (vWF; rabbit IgG; Sigma) and endothelial NO-synthetase (eNOS; mouse IgG1; BD Pharmingen) followed by respective secondary Ab against goat IgG-AlexaFluor-555 (red fluorescence), rabbit IgG-AlexaFluor-488 (green fluorescence) and mouse IgG-AlexaFluor-488 conjugates (Molecular Probes). Negative controls were done using appropriate primary IgG controls (Sigma). Cell nuclei were visualized by DAPI staining (blue fluorescence). Fluorescent images were composed using Adobe Photoshop software. Ac-LDL uptake was assessed by incubation with DiI-Ac-LDL conjugate. Scale bar is 50 µm.

Kinetic analysis of CFC emergence demonstrated that E-CFCs were induced on day 4 of culture, the day following the appearance of CD34+ cells (FIG. 9B). Myeloid (GM, M) and mixed (GEMM) CFCs appeared later, along with the induction of CD43 and CD41a expression on CD34+ cells. After day 7 of culture, we observed predominant expansion of myeloid CFCs and gradual decrease of E-CFCs and GEMM-CFCs (FIG. 9B). As shown in FIG. 4, transcription factors associated with hematopoiesis such as SCL, GATA-1, and GATA-2 were not expressed in undifferentiated hES cells. GATA-1 and GATA-2 were detected on days 2-3 of hES cell differentiation, coincident with the appearance of CD34+ cells, while SCL expression was detected a day later. GATA-2 and SCL expression peaked on days 4-6 of differentiation and then gradually decreased, while GATA-1 expression gradually increased up to day 10 of culture (see FIG. 11). PCR analysis demonstrated that undifferentiated hES cells already expressed several genes essential for hematopoietic development, such as Flk-1 and Flt-3. However, at least two major waves of Flk-1 and Flt-3 upregulation that were coincident with the appearance of CD34+ (days 3-4) and CD45+ cells (days 7-9) were observed in hES cells/OP9 co-cultures (FIG. 11).

These data clearly demonstrated that the OP9 bone marrow stromal cell line efficiently induced hematopoietic differentiation of hES cells and reproduced early stages of hematopoietic development.

Isolated hES Cell-Derived CD34+ Cells are Highly Enriched in Cells with Phenotypic and Functional Hematopoietic Properties Since CD34 is considered to be the most reliable marker for embryonic and adult hematopoietic stem cells (Sutherland D R, et al., *Stem Cells* 1993; 11:50-57; Rappold I, et al., *Blood* 1997; 90:111-125; Oberlin E, et al., *Development* 2002; 129:4147-4157), we examined whether hematopoietic progenitors would arise in CD34+ population in the OP9 co-culture. Using the magnetic separation technique, we were able to obtain up to $10^7$ CD34+ cells with more than 95% purity from a similar number of the initially plated hES cells after 8-9 days of culture (Table 3; FIG. 12). CD34+ selection markedly enriched all CFCs, except E-CFCs. The most significant enrichment was seen for the multilineage progenitors, GEMM-CFCs. All GEMM-CFCs were found within the CD34+ population, and none were found within the CD34− population. The CD34− population contained minimal numbers of M-CFC and GM-CFCs (FIG. 12C). The levels of SCL, Flk-1, GATA-1, and GATA-2 expression by QPCR were substantially higher within the CD34+ population as compared to the CD34− population (FIG. 12B). These results demonstrated that hES cell-derived hematopoietic progenitors were restricted mostly to the CD34+ population.

Bone marrow multipotential hematopoietic cells possess the ability to efflux dyes such as Hoechst 33342 and Rhodamine 123 (Rho) (Baum C M, et al., *Proceedings of the National Academy of Sciences of the United States of America.* 1992; 89:2804-2808; Goodell M A, et al., *Nature Medicine* 1997; 3:1337-1345; Uchida N, et al., *Blood* 1996; 88:1297-1305) and express a high level of ALDH (Jones R J, et al., *Blood* 1995; 85:2742-2746; Storms R W, et al., *Proceedings of the National Academy of Sciences of the United States of America.* 1999; 96:9118-9123). We found that cells with the verapamil-sensitive ability to efflux Rho constituted a minor but consistent fraction of CD34+CD45+ cells (FIG. 12D). Rho-effluxing cells were not found within either the CD34+CD45− subset (see FIG. 12D) or undifferentiated hES cells (not shown). In addition, cells rich in ALDH activity were identified within isolated CD34+ cells, predominantly within the CD34+CD45+ subset (FIG. 12E).

Figure 13A:
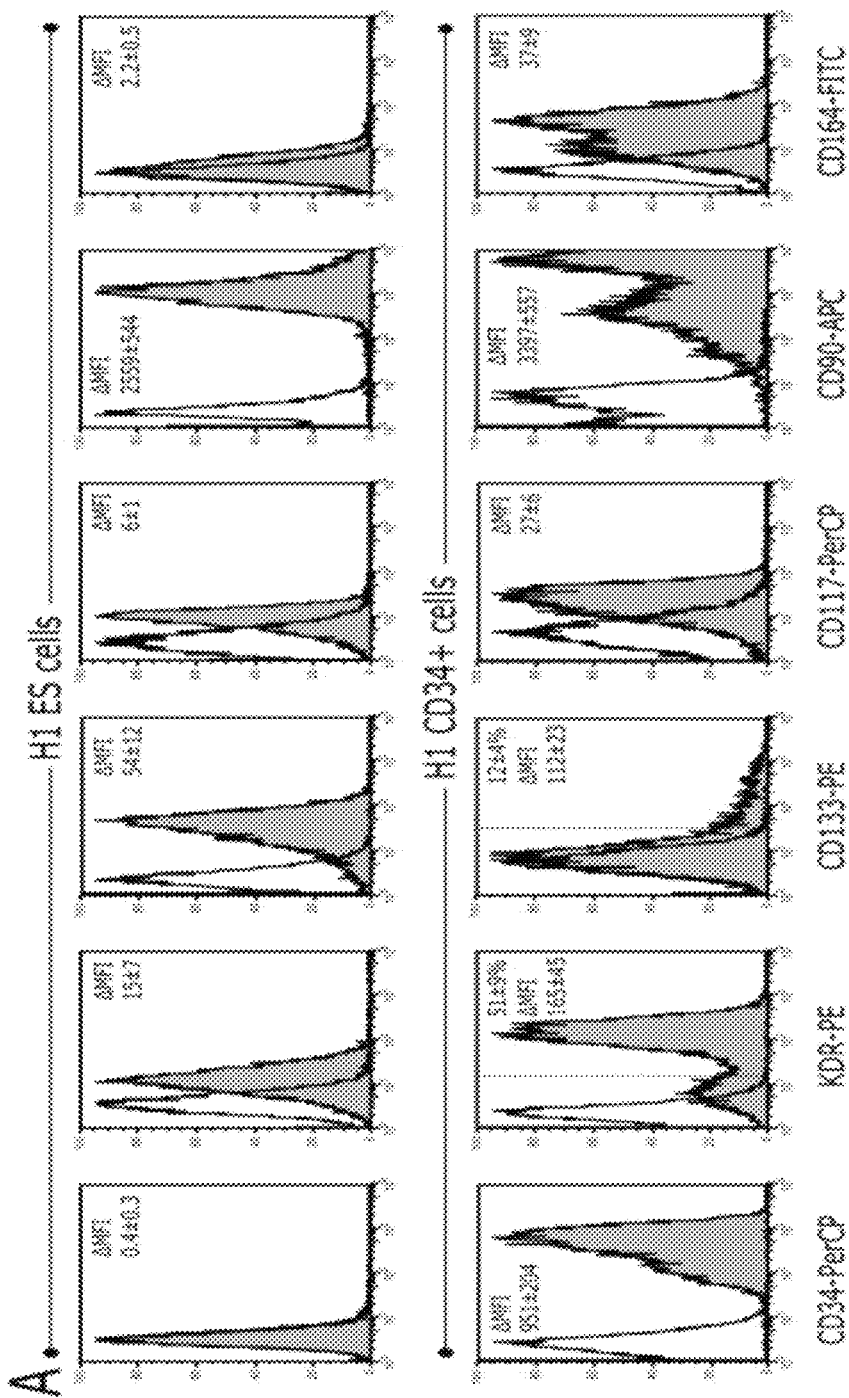

Several molecules, such as CD90, CD117, and CD133, which are known to be expressed on primitive hematopoietic progenitors, (Rappold I, et al., *Blood* 1997; 90:111-125; Baum C M, et al., *Proceedings of the National Academy of Sciences of the United States of America.* 1992; 89:2804-2808; Briddell R A, et al., *Blood* 1992; 79:3159-3167; Yin A H, et al., *Blood* 1997; 90:5002-5012) were found to be expressed on undifferentiated hES cells (FIG. 13A). The hES cell-derived CD34+ cells up-regulated expression of CD90, CD117, CD164, but down-regulated the expression of CD133 (FIG. 13A). Most of the CD34+ cells were CD31+ and CD38− (Table 3, FIGS. 10 and 14C). A significant proportion of CD34+ cells co-expressed vascular endothelial growth factor receptor 2 (VEGFR2 or KDR, FIG. 13A). CD45−, CD41a−, CD43−, and CXCR4-positive subsets were identified within CD34+ cells (see Table 3, FIG. 10). Like the CD34+ primitive hematopoietic progenitors that arise in the human embryo, (Oberlin E, Tavian M, Blazsek I, Peault B. Blood-forming potential of vascular endothelium in the human embryo. Development. 2002; 129:4147-4157) hES cell-derived CD34+ cells did not express lineage-specific markers CD3, CD19, and CD14 (data not shown).

Undifferentiated hES cells and MACS-selected hES cell-derived CD34+ cells were stained with Wright solution and examined microscopically (FIGS. 13B and 13C). Morphologically, at least two major subpopulations of cells can be identified within hES cell-derived CD34+ cells. A majority of the CD34+ cells had a high nuclear cytoplasmic ratio, dark blue cytoplasm, and a nucleus with two or three large nucleoli, and they resembled bone marrow hematopoietic blast cells (FIG. 13C, left panel). The second, smaller population consisted of cells with an abundant light-blue cytoplasm and a relatively small nucleus with inconspicuous nucleoli (FIG. 13C, right panel). This population may have represented endothelial precursors. Both subpopulations of isolated CD34+ cells were considerably different from undifferentiated hES cells, which on cytospins tended to form clumps composed of large cells with vacuolated cytoplasms and an irregular hyperchromatic nuclei (FIG. 13B). In contrast to undifferentiated hES cells, CD34+ cells expressed neither Oct-4 transcription factors specific for totipotent ES cells (Pesce M, et al., *Stem Cells* 2001; 19:271-278) (FIG. 13D) nor TRA-1-60 and TRA-1-81 hES cell markers (Thomson J A, et al., *Science* 1998; 282:1145-1147). These findings indicate advanced differentiation of CD34+ cells and rule out contamination of isolated CD34+ cells by undifferentiated hES cells.

hES Cell-Derived CD34+ Cells Produce Both Lymphoid and Myeloid Cells Upon Co-Culture with MS-5 Stromal Cells To demonstrate the lympho-myeloid potential of hES cell-derived hematopoietic progenitors, we cultured isolated CD34+ cells on MS-5 stromal cell line, which supports myeloid and B-lymphoid human hematopoiesis (Robin C, et al., *J Exp Med.* 1999; 189:1601-1610; Berardi A C, et al., *Blood* 1997; 89:3554-3564; Tavian M, et al., *Immunity* 2001; 15:487-495). During MS-5 co-culture CD34+ cells developed adherent hematopoietic colonies as well cobblestone-like colonies under the stroma first detected on day 7 of co-culture (FIG. 14A). After 21 days, a large population of CD45+ cells (58.5±3.4% of total cells in co-culture) was detected by flow cytometry and granulocytes, macrophages, and lymphoid cells were identified morphologically on cytospins. The CD45+ population included CD14+HLA-DR+ macrophages (FIG. 14B), CD10+CD66b+ mature granulocytes (FIG. 14C), CD56+ NK cells (FIG. 14D), and CD19+ B cells (FIG. 14E).

To further prove that the CD56+ population represents NK cells, we added to some cultures IL-15, which induces maturation of NK precursors into perforin-positive cytolytic NK cells (Ye W, et al., *Cell Immunol.* 1996; 174:54-62; Mingari M C, et al., *Eur J Immunol.* 1997; 27:1374-1380; Leclercq G, et al., *J Exp Med.* 1996; 184:325-336). As shown in FIG. 14F, perforin-expressing CD56+ NK cells were generated in cultures with IL-15. CD56-Perforin+ cells were also detected when cells were cultured with IL-15. These cells may represent immature macrophage precursors that have been shown to acquire perforin expression upon IL-2 stimulation (Li H, et al., *J Leukoc Biol.* 1994; 56:117-123). In addition, in CD34+/MS-5 co-cultures, we detected CD3ε, CD3δ, and CD3ζ transcripts, which are known to be expressed in embryonic and fetal NK cells, (Phillips J H, et al., *J Exp Med.* 1992; 175:1055-1066) as well as mRNAs for VpreB and Iga (CD79a or mb-1) components of pre-B cell receptor complex (FIG. 14G). We found very low, but consistent expression of CD3γ in CD34+/MS-5 co-culture, however, pre-Tα, a component of the pre-T cell receptor complex was not detected by PCR. Thus, the lymphopoiesis in CD34+/MS-5 co-culture is mostly restricted to NK and B cell lineages and a different culture system is required to direct the differentiation of CD34+ cells into T lymphocytes. Altogether, these results provide strong evidence that, CD34+ cells generated in hES/OP9 co-culture possess the capacity to generate both lymphoid and myeloid cells.

TABLE 2

Sequence of human gene-specific primers used for PCR

| Gene | Forward primer (5'-3') | SEQ ID NO | Reverse primer (5'-3') | SEQ ID NO | Amplicon (bp) |
|---|---|---|---|---|---|
| CD3δ | TTCCGGTACCTGTGAGTCAGC | SEQ ID NO: 1 | GGTACAGTTGGTAATGGCTGC | SEQ ID NO: 17 | 636 |
| CD3ε | AGTTGGCGTTTGGGGGCAAGATGGTAATGAAGAAA | SEQ ID NO: 2 | CCCAGGAAACAGGGAGTCGCAGGGGGACTGGAGAG | SEQ ID NO: 18 | 640 |
| CD3γ | GGGCTGCTCCACGCTTTTGC | SEQ ID NO: 3 | TTTTCCCCAATAGGTGGCGC | SEQ ID NO: 19 | 817 |
| CD3ζ | CTCTGCCTCCCAGCCTCTTT | SEQ ID NO: 4 | GCGTCGTAGGTGTCCTTGGT | SEQ ID NO: 20 | 481 |
| CD45 | TTAACTTATACCCTTCGTGTC | SEQ ID NO: 5 | CCTGCTTTACTTTGTCCACTTC | SEQ ID NO: 21 | 400 |
| Flk-1 | ATGCACGGCATCTGGGAATC | SEQ ID NO: 6 | GTCACTGTCCTGCAAGTTGCTGTC | SEQ ID NO: 22 | 573 |
| Flt-3 | CAAGTGCTGTGCATACAATTCCC | SEQ ID NO: 7 | ACCTGTACCATCTGTAGCTGG | SEQ ID NO: 23 | 210 |
| GAPDH | TCCAAAATCAAGTGGGGCGAT | SEQ ID NO: 8 | TTCTAGACGGCAGGTCAGGTC | SEQ ID NO: 24 | 475 |
| GATA-1 | CTCCCTGTCCCCAATAGTGC | SEQ ID NO: 9 | GTCCTTCGGCTGCTCCTGTG | SEQ ID NO: 25 | 520 |
| GATA-2 | GCTTCCCTCTCTGAAATAGCCGAA | SEQ ID NO: 10 | CAGAATCTAAGCTCGGGACACGTT | SEQ ID NO: 26 | 771 |
| GATA-3 | TGCAGGAGCAGTATCATGAAGCCT | SEQ ID NO: 11 | CGATCAAACAACTGTGGCCAGTGA | SEQ ID NO: 27 | 406 |
| mb-1 | TCCAAGCTCTGCCTGCCACCAT | SEQ ID NO: 12 | GACTGCTGGTATGACTCGTTGC | SEQ ID NO: 27 | 330 |
| Pre-Tα | AGTACACAGCCCATGCATCTGTCA | SEQ ID NO: 13 | AATGCTCCAAGACTGGAGGAAGGA | SEQ ID NO: 29 | 445 |
| SCL | ATGGTGCAGCTGAGTCCTCC | SEQ ID NO: 14 | TCTCATTCTTGCTGAGCTTC | SEQ ID NO: 30 | 331 |
| VpreB | TTTGTCTACTGCACAGGTTGTGG | SEQ ID NO: 15 | TGCAGTGGGTTCCATTTCTTCC | SEQ ID NO: 31 | 386 |
| βActin | TGACGGGGTCACCCACACTGTGCCCATCTA | SEQ ID NO: 16 | CTAGAAGCATTGCGGTGGACGATGGAGGG | SEQ ID NO: 32 | 650 |

TABLE 3

Sorting and phenotype of H1-derived CD34+ cells.

| Parameter | Mean ± SD (n = 9) |
|---|---|
| hES (H1) cells plated (×10⁶) Presort cells | 8.4 ± 1.4 |
| absolute number (×10⁶) | 82.7 ± 22.4 |
| % CD34 | 12.8 ± 4.7 |
| Sorted CD34+ cells | |
| absolute number (×10⁶) | 8.7 ± 3.8 |
| purity (%) | 97.1 ± 0.8 |
| recovery (%)* | 84.5 ± 6.2 |
| Phenotype of CD34+ cells (%) | |
| CD31 | 88.5 ± 3.5 |
| CD41a | 20.1 ± 10.3 |
| CD43 | 37.8 ± 10.1 |
| CD45 | 14.2 ± 8.6 |
| CD38 | 0.6 ± 0.8 |
| CD184 (CXCR4) | 35.2 ± 23.2 |

*% recovery = (absolute number of CD34+ cells in CD34+ fraction/absolute number of CD34+ cells in presort fraction) × 100

TABLE 4

CFC potential and phenotype of H1-derived CD34+ cells after in vitro culture in serum-free and serum-containing media.*

| Parameter | Sorted CD34+ cells | Feeder-free in vitro culture | |
|---|---|---|---|
| | | SFEM | αMEM + 10% FBS |
| Expansion (×fold) | | | |
| total cells | | 4.6 ± 2.2 | 5.2 ± 1.5 |
| total CFCs | | 2.4 ± 1.3 | 4.3 ± 1.8 |
| CFCs (abs. number/10⁶ cells) | | | |
| E-CFC | 640 ± 320 | 0 | 0 |
| GEMM-CFC | 3400 ± 550 | 300 ± 220 | 0 |
| GM-CFC | 4850 ± 1300 | 1600 ± 340 | 1500 ± 520 |
| M-CFC | 9950 ± 1200 | 8800 ± 1500 | 15500 ± 6170 |
| Phenotype (%) | | | |
| CD34 | 98.6 ± 1.5 | 69.2 ± 11.2 | 24.9 ± 10.5 |
| CD45 | 12.6 ± 2.3 | 95.2 ± 7.3 | 97.8 ± 2.1 |
| CD38 | 0.6 ± 0.4 | 1.8 ± 0.9 | 76.0 ± 9.4 |

*Data presented as mean ± SD (n = 3).

D. Discussion

Our study represents the first report that describes hematopoietic differentiation of hES cells using the OP9 bone stromal cell line. The OP9 co-culture has been used successfully for hematopoietic differentiation of mouse and non-human primate ES cells and to obtain multilineage hematopoietic progenitors as well as mature hematopoietic cells such as lymphocytes and megakaryocytes, which cannot be obtained using the embryoid body method (Nakano T, et al., *Science* 1994; 265:1098-1101; Nakano T, et al., *Science* 1996; 272:722-724; Eto K, et al., Proceedings of the National Academy of Sciences of the United States of America. 2002; 99:12819-12824; Umeda K, et al., *Development* 2004; 131:1869-1879). Differentiation of hES cells through OP9 co-culture was very similar to that observed previously in murine ES cell/OP9 co-culture (Nakano T, et al., *Science* 1996; 272:722-724; Kitajima K, et al., *Methods in Enzymology* 2003; 365:72-83). Mesodermal colonies appeared at day 4 of culture, and the first CFCs were detected on days 4-5 of culture with decrease of E-CFCs on days 8-9 of culture. Formation of mesodermal-type colonies in the OP9 co-culture can be observed under the microscope. Single-cell suspension of hES cells growing on OP9 cells can be easily obtained by mild enzymatic digestion and analyzed by flow-cytometry and CFC assay. In the OP9 co-culture, the peak of hematopoietic differentiation occurred at least one week earlier (days 7-9 of culture) when compared to the embryoid body method and S17 co-culture (days 15-22 of culture) (Kaufman D S, et al., Proceedings of the National Academy of Sciences of the United States of America. 2001; 98:10716-10721; Chadwick K, et al., *Blood* 2003; 102:906-915). In contrast to the 517 or MS-5 co-culture, hES cells differentiated on OP9 cells gave rise to CD34+CD45+ cells and produced a much higher number of CFCs (Kaufman D S, et al., Proceedings of the National Academy of Sciences of the United States of America. 2001; 98:10716-10721; Lu S J, et al., *Blood* 2004). However, OP9 cells are very sensitive to variations in maintenance conditions including medium source and serum lot, which can affect the ability of OP9 cells to support hematopoiesis.

The strong hematopoiesis-promoting activity of OP9 is at least partially attributed to the lack of M-CSF production, (Kitajima K, et al., *Methods in Enzymology* 2003; 365:72-83) since M-CSF inhibits early hematopoiesis (Minehata K, et al., *Blood* 2002; 99:2360-2368). However, murine M-CSF is not active on human cells, (Das S K, et al., *J of Biological Chemistry* 1982; 257:13679-13684) and therefore, should not be a factor, which explain differences in the efficiency of hES cell hematopoietic differentiation through co-culture with various mouse bone marrow stromal cell lines. We think that the recently identified mKirre protein (Ueno H, et al., *Nat. Immunol.* 2003; 4:457-463), differences in expression of Notch ligands, or other unidentified factors, rather than lack of M-CSF production, are accountable for the distinct hemogenic properties of OP9 cells.

CD34+ cells derived through the OP9 co-culture were highly enriched in clonogenic progenitors. The CFC frequency in hES cell-derived CD34+ cells (approximately 4%) was comparable with the CFC frequency in human bone marrow CD34+ cells (Rappold I, et al., *Blood* 1997; 90:111-125; de Wynter E A, et al., *Stem Cells* 1998; 16:387-396; Strauss L C, et al., *Exp Hematol.* 1986; 14:878-886), and the lack of E-CFC enrichment by CD34+ selection is consistent with the progressive loss of CD34 expression by erythroid progenitors with advanced maturation (Strauss L C, et al., *Exp Hematol.* 1986; 14:878-886). As expected, CD34+ population expressed much higher levels of SCL, GATA-1, GATA-2, Flk-1, and CD45, as compared to CD34− cells. A lower level of Flt-3 expression in CD34+ cells was consistent with their the most primitive hematopoietic progenitor features (Rappold I, et al., *Blood* 1997; 90:111-125).

Hematopoietic stem cells can be identified based on the efflux of fluorochrome dyes such as Rho and Hoechst 33342 (Baum C M, et al., Proceedings of the National Academy of Sciences of the United States of America. 1992; 89:2804-2808; Goodell M A, et al., *Nature Medicine* 1997; 3:1337-1345; Uchida N, et al., *Blood* 1996; 88:1297-1305) and by a high level of ALDH expression (Jones R J, et al., *Blood* 1995; 85:2742-2746; Storms R W, et al., Proceedings of the National Academy of Sciences of the United States of America. 1999; 96:9118-9123). Dye-excluding and ALDH$^{bright}$ bone marrow cells are highly enriched for repopulating cells and are present in multiple species (Goodell M A, et al., *Nature Medicine* 1997; 3:1337-1345; Spangrude G J, et al., Proceedings of the National Academy of Sciences of the United States of America. 1990; 87:7433-7437; Jones R J, et al., *Blood* 1996; 88:487-491; Hess D A, et al., *Blood* 2004). Similar to bone marrow CD34+ cells, the Rho efflux in hES cell-derived CD34+ cells was inhibited by verapamil, pointing to P-glycoprotein-mediated transport. The finding of Rho-extruding cells and ALDH$^{bright}$ cells within hES cell-derived CD34+ cells suggested that these cells may contain a subpopulation with hematopoietic stem cell activity.

Here we demonstrated lympho-myeloid differentiation of hES cells which, so far, has not been reported. The ability to generate, simultaneously, lymphoid and myeloid progenitors is considered a distinctive feature of stem cells having definitive hematopoietic potential. In humans, lympho-myeloid progenitors have been found in paraaortic splanchnopleura, while yolk sac hematopoietic cells have been restricted to myelopoiesis (Robin C, et al., *J Exp Med.* 1999; 189:1601-1610; Berardi A C, et al., *Blood* 1997; 89:3554-3564; Tavian M, et al., *Immunity* 2001; 15:487-495). These data indicate that hES cell/OP9 co-culture recapitulates major events observed during embryonal hematopoietic development, including formation of lympho-myeloid progenitors that can be found within para-aortic splanchnopleura.

The hallmark of hematopoietic stem cells is their capacity to establish long-term multilineage engraftment. Recently, hematopoietic cells able to be engrafted in conditioned adult mice have been derived from mouse ES cells transduced with Bcr/Abl or HoxB4 (Kyba M, et al., *Cell.* 2002; 109:29-37; Perlingeiro R C, et al., *Development* 2001; 128:4597-4604). So far, no engraftment of hES cell-derived hematopoietic cells has been reported. The lack of a system for producing large numbers of hES cell-derived hematopoietic precursors has, at least in part, delayed engraftment studies of hES cells. The OP9 co-culture allowed us to obtain CD34+ cells highly enriched in hematopoietic progenitors in sufficient quantities for genetic manipulation as well as for transplantation in immunodeficient mice.

In summary, our data clearly indicate that CD34+ populations obtained by differentiation of hES cells in co-culture with OP9 cells are enriched in cells with features of hematopoietic progenitors and stem cells. Preliminary in vivo engraftment experiments are underway in our laboratory to prove that cells with hematopoietic stem cell potential can be generated from hES cells.

We claim:

1. A purified population of CD34+ CD43+ CD45+ CD41 a− CD235a− cells, wherein the cells are prepared by a method comprising:
    (a) preparing a culture of macrophage colony-stimulating factor (M-CSF) deficient stromal cells;
    (b) adding human embryonic stem (ES) cells to said culture in medium supplemented with serum;
    (c) culturing said ES cells until the culture begins to express CD45;
    (d) isolating cells that are both CD34+ cells and CD43+ from the resulting culture; and
    (e) separating CD45+ CD41 a− CD235a− cells from the isolated cells of step (d), wherein greater than 95% of the cells separated in (e) are CD34+ CD43+ CD45+ CD41 a− CD235a− cells.

2. A cell culture comprising the purified population of cells of claim 1.

3. A method for generating a population of CD34+ CD43+ CD45+ cells comprising the steps of:
    (a) preparing a culture of macrophage colony-stimulating factor (M-CSF) deficient stromal cells;
    (b) adding human ES cells to said culture in medium supplemented with serum;
    (c) culturing said ES cells until the culture begins to express CD45;
    (d) isolating cells that are both CD34+ and CD43+ cells; and
    (e) separating CD45+ CD41 a− CD235a− cells from the isolated cells of step (d), wherein greater than 95% of the cells separated in (f) are CD34+ CD43+ CD45+ CD41 a− CD235a− cells.

* * * * *

UNITED STATES PATENT AND TRADEMARK OFFICE
CERTIFICATE OF CORRECTION

PATENT NO. : 9,624,470 B2
APPLICATION NO. : 13/194623
DATED : April 18, 2017
INVENTOR(S) : Igor I. Slukvin et al.

It is certified that error appears in the above-identified patent and that said Letters Patent is hereby corrected as shown below:

In the Specification

Column 5, Line 18 - "OE CD235a-OE" should be -- PE CD235a-PE --
Column 22, Line 21 - "CD43+CD45-/+Lin- cells" should be -- CD43+CD45-Lin- cells --
Column 32, Line 57 - "and Iga" should be -- and Igα --

Signed and Sealed this
Twenty-third Day of April, 2019

Andrei Iancu
*Director of the United States Patent and Trademark Office*